US010480982B2

(12) United States Patent
Parrott et al.

(10) Patent No.: US 10,480,982 B2
(45) Date of Patent: Nov. 19, 2019

(54) ACOUSTIC CALIBRATION ARRAY FOR TANKS AND VESSELS

(71) Applicant: Saudi Arabian Oil Company, Dhahran (SA)

(72) Inventors: Brian Parrott, Thuwal (SA); Fadl Abdellatif, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 282 days.

(21) Appl. No.: 15/491,588

(22) Filed: Apr. 19, 2017

(65) Prior Publication Data

US 2018/0306628 A1   Oct. 25, 2018

(51) Int. Cl.
*G01F 17/00* (2006.01)
*G05D 1/02* (2006.01)
(Continued)

(52) U.S. Cl.
CPC .......... *G01F 17/00* (2013.01); *G01N 29/043* (2013.01); *G01N 29/07* (2013.01); *G01N 29/223* (2013.01);
(Continued)

(58) Field of Classification Search
USPC ........................................................... 73/149
See application file for complete search history.

(56) References Cited

U.S. PATENT DOCUMENTS 5,456,114 A    10/1995  Liu et al.
6,573,732 B1 *  6/2003  Reimer ............... B60K 15/077
                                              324/644

(Continued)

FOREIGN PATENT DOCUMENTS

EP    0621462 A2    10/1994
EP    2115386 A1    11/2009

OTHER PUBLICATIONS

Lemmon. "Trimble Navigation Limited, Oil, Gas, and Chemical Division." Tank Inspection and Calibration With 3D Laser Scanning Introduction. Oct. 1, 2011 (Oct. 1, 2011), XP055479584, Retrieved from the Internet on May 30, 2018. 7 pages.

(Continued)

*Primary Examiner* — Clayton E. LaBalle
*Assistant Examiner* — Warren K Fenwick
(74) *Attorney, Agent, or Firm* — Leason Ellis LLP

(57) ABSTRACT

A system and method is disclosed for calibrating the volume of storage containers using mechanical or acoustic wave-based inspection techniques. The exemplary calibration system comprises an array of measurement devices controllably deployed in respective positions on the outside surface of the container. The measurement devices include a transducer for sending signals along the surface of the container and sensors configured to detect the signals. The measurement devices are in communication with a diagnostic computing device that controls the positioning and the operation of the measurement devices and is further configured to determine the time time-of-flight of the signals that travel between the various devices. Moreover, according to the specific arrangement of the measurement devices and the measured signal information, the control computer is configured to calculate the dimensions of the container and its internal volume.

20 Claims, 17 Drawing Sheets

(51) Int. Cl.
  *G01N 29/04* (2006.01)
  *G01N 29/07* (2006.01)
  *G01N 29/22* (2006.01)
  *G01N 29/265* (2006.01)
  *G01N 29/34* (2006.01)
(52) U.S. Cl.
  CPC ......... *G01N 29/265* (2013.01); *G01N 29/343* (2013.01); *G05D 1/0255* (2013.01); *G01N 2291/011* (2013.01); *G01N 2291/02854* (2013.01); *G01N 2291/0427* (2013.01); *G01N 2291/102* (2013.01); *G01N 2291/103* (2013.01); *G01N 2291/105* (2013.01); *G01N 2291/2634* (2013.01); *G01N 2291/2695* (2013.01)

(56) References Cited

U.S. PATENT DOCUMENTS

| | | | |
|---|---|---|---|
| 6,925,870 B2 * | 8/2005 | Pappas | G01F 23/2962 73/290 V |
| 7,216,536 B2 | 5/2007 | Young et al. | |
| 7,373,839 B2 * | 5/2008 | Wiest | G01F 1/662 73/861.23 |
| 10,036,763 B2 * | 7/2018 | Hies | G01P 5/244 |
| 2002/0088281 A1 | 7/2002 | Gorman et al. | |
| 2012/0281096 A1 * | 11/2012 | Gellaboina | G01F 23/292 348/163 |
| 2014/0345375 A1 | 11/2014 | Hassell, Jr. | |
| 2016/0041024 A1 * | 2/2016 | Reimer | G01F 23/2962 73/290 V |
| 2016/0320219 A1 | 11/2016 | Hellevang et al. | |
| 2016/0320226 A1 * | 11/2016 | Schaefer | G01F 23/2962 |
| 2017/0010146 A1 * | 1/2017 | Kassubek | G01N 29/222 |
| 2017/0102362 A1 * | 4/2017 | Sackmann | B01L 3/0268 |
| 2019/0011304 A1 * | 1/2019 | Cunningham | G01F 17/00 |

OTHER PUBLICATIONS

International Search Report and Written Opinion in corresponding International Patent Application No. PCT/2018/023316, dated Jun. 14, 2018. 16 pages.

* cited by examiner

ACOUSTIC CALIBRATION ARRAY FOR TANKS AND VESSELS

FIELD OF THE INVENTION

The present invention relates to systems and methods for non-destructive testing of structures, in particular to systems and methods for acoustic measurement of the geometry of containers in a non-destructive manner.

BACKGROUND

In the oil and gas industry the storage tanks for crude and refined products play a key part in the supply chain of hydrocarbons. Knowing the exact volume of these storage units plays a critical role when transferring products to and/or from the tanks. As a result of variations in external and internal conditions (i.e. temperature) and aging and also as a result of the weight of the liquid product (i.e. hydrostatic pressure), the tank volume can vary by as much as +/−0.2%. Considering a 250,000 barrel storage tank, this variation would result in a volume of +/−500 barrels in volume change.

As a result of the high value of petroleum hydrocarbons, there is a mandatory requirement for calibration of storage tanks. Tanks used for custody transfer must be calibrated such that the transferred volume is very accurately known (eg. Less than 0.1% error). The most commonly used techniques to perform this are; manual strapping (API MPMS 2.2A), optical techniques (Optical Reference Line Method ORLM—API Chapter 2.2B, Optical Triangulation Method (OTM)—API Chapter 2.2C, Electro-Optical Distance Ranging Method (EODR)—API Chapter 2.2D) and liquid calibrations (API Standard 2555). However, these measurements have been found to produce errors and are considered non-effective. In some cases, the foregoing testing techniques require tank downtime (e.g., emptying of the tank or otherwise halting the tank operation temporarily), which accumulates additional costs to the losses incurred. Moreover, many of the foregoing testing techniques are invasive in that they require accessing the internal volume of the tank and also can be destructive.

In the oil and gas industry, ultrasonic probes have been used to determine the health and structural integrity of pipelines and vessels at localized points. Known systems for measuring wall thickness using ultrasound are based on the concept of using the time-of-flight (TOF) for sound to travel between the outer and inner surfaces of the wall to determine distance traveled. In such implementations, the TOF analysis of the ultrasonic pulses return journey through the metallic medium (i.e. pipe or vessel) is used to determine the thickness of the wall and, thus, degradation as a result of corrosion. Similarly, there has been work on sending acoustic waves along the length of pipes to determine if there are cracks or other anomalies that would cause unexpected reflections. However, such systems are reliant on known or assumed pipe dimensions and are not configured to determine the geometric profile of the pipe. Rather, the geometric measurement of the container is assumed or determined using the known alternative methods mentioned above.

In the case of tank inspection, the aforementioned methods require high levels of calibration and also require a couple of days' worth of work (e.g., including the erection and use of high scaffolding to deploy the measuring systems and conduct the measurements). Therefore, calibration/measurement of the tanks is done infrequently, leading to erroneous tank volumes and lost sales revenue.

The existing methods for tank calibration present significant drawbacks. For instance, using the current standards, it can take 1-2 days of work to perform the calibration. As a result, calibration of storage tanks is performed infrequently thus leading to inaccurate measurements of the actual volume stored within the tank or transferred to and from the tank, which can be costly. For example, a traditional timeframe between calibrations can be between five and fifteen years.

What is needed are systems and methods for calibrating the volume of storage tanks that addresses the limitations associated with the efficiency of performing calibration using existing systems. More specifically, what is needed are systems and methods for accurately performing tank calibration that can be deployed and operated in a relatively quick, low-cost, and non-invasive manner. What is also needed is a system that can be deployed quickly and on-demand and thus facilitates detection of changes in tank volume on a more frequent basis (e.g., on a daily basis or even per-fill basis).

It is with respect to these and other considerations that the disclosure made herein is presented.

SUMMARY

According to an aspect of the present invention, there is provided a method for measuring a volume of a storage container using a plurality of acoustic devices including a transducer and one or more sensors. The method includes the steps of deploying the plurality of acoustic devices into respective positions on an exterior surface of a circumferential wall of the storage container. More specifically, the one or more sensors are acoustically coupled to the surface and configured to detect pulses propagating along the surface. Likewise, the transducer is acoustically coupled to the surface and is configured generate one or more pulses that radiate along the surface away from the transducer and toward the one or more sensors in at least a first circumferential path and a second circumferential path. The method also includes the step of generating one or more pulses using the transducer, wherein each pulse is generated at an impulse time. In addition, the method includes the step of detecting, using the one or more sensors, the one or more pulses radiating along the first circumferential path and the second circumferential path and recording a respective time that the one or more pulses radiating along a respective circumferential path are detected. The method also includes the step of calculating, by a computing device that is in electronic communication with the one or more sensors respective times of flight (TOFs) for the one or more pulses. More specifically, the TOFs are calculated based on the impulse time and respective detection times and each respective TOF is an elapsed time for the pulse to travel between two of the acoustic devices along a particular circumferential path. The method also includes the step of calculating, with the computing device, respective distances between the acoustic devices in each of the first and second circumferential directions based on the respective TOFs and a speed of sound through the wall. Lastly, the method includes the step of determining, with the computing device, the volume of the storage container based on the calculated respective distances.

According to a further aspect of the present invention, there is provided a system for measuring a volume of a storage container. The system comprises a plurality of acoustic devices that are configured to be deployed at respective positions on an exterior surface of a circumferential wall of the container. In particular, the acoustic devices include a plurality of sensors that are configured to be acoustically coupled to the circumferential wall and also to detect pulses that are radiating along the surface. Also included among the acoustic devices is a transducer that is configured to be acoustically coupled to the surface and generate one or more pulses that radiate along the surface away from the transducer and toward the plurality of sensors along respective circumferential paths.

The system also includes a computing system that comprises a non-transitory computer readable storage medium and one or more processors in electronic communication with the plurality of acoustic devices and the computer readable storage medium. The computing system also includes one or more software modules comprising executable instructions that are stored in the storage medium and are executable by the processor. In particular, the software modules include a signal control module that configures the processor to, using the transducer, generate one or more pulses using the transducer at respective impulse times. In addition, the signal control module further configures the processor to, using the sensors, detect the arrival of the one or more pulses at the sensors, respectively, and record respective detection times. Also included among the software modules is a signal analysis module that configures the processor to calculate, based on the respective impulse times and respective detection times, respective times of flight (TOFs) for the one or more pulses. More specifically, the respective TOFs are an elapsed time for the pulse to travel between two of the acoustic devices along a respective circumferential path. Also included among the software modules is a geometric analysis module that configures the processor to calculate distances between the acoustic devices based on the respective TOFs and a speed of sound through the wall, and to calculate the volume of the storage container based on the calculated distances.

According to a still further aspect of the present invention, there is provided another system for measuring a volume of a storage container. The system comprises a plurality of acoustic devices that are configured to be deployed at respective positions on an exterior surface of a circumferential wall of the container. In particular, the acoustic devices include a plurality of sensors that are configured to be acoustically coupled to the circumferential wall and also to detect pulses that are radiating along the surface. Also included among the acoustic devices is a transducer that is configured to be acoustically coupled to the surface and generate one or more pulses that radiate along the surface away from the transducer and toward the plurality of sensors along respective circumferential paths. The system also includes a robot that is configured to deploy one or more of the acoustic devices on the surface of the circumferential wall. More specifically, the robot includes a drive system and one or more position sensors for monitoring a position of the robot. Further, the robot is configured to controllably deploy the one or more sensors at the respective positions on the surface.

Systems in accordance with particular implementations can further include a computing system that comprises a non-transitory computer readable storage medium and one or more processors in electronic communication with the plurality of acoustic devices, the robot and the computer readable storage medium. The computing system also includes one or more software modules comprising executable instructions that are stored in the storage medium and are executable by the processor. In particular, the software modules include a signal control module that configures the processor to, using the transducer, generate one or more pulses using the transducer at respective impulse times. In addition, the signal control module further configures the processor to, using the sensors, detect the arrival of the one or more pulses at the sensors, respectively, and record respective detection times. Also included among the software modules is a signal analysis module that configures the processor to calculate, based on the respective impulse times and respective detection times, respective times of flight (TOFs) for the one or more pulses. More specifically, the respective TOFs are an elapsed time for the pulse to travel between two of the acoustic devices along a respective circumferential path. Also included among the software modules is a geometric analysis module that configures the processor to calculate distances between the acoustic devices based on the respective TOFs and a speed of sound through the wall, and to calculate the volume of the storage container based on the calculated distances. In addition, the software modules include a position control module that configures the processor to, using the robot, iteratively adjust the respective position of one or more of the acoustic devices on the surface and re-calculating respective TOFs until at least two of the acoustic devices are aligned in one of a transverse direction and a longitudinal direction. More specifically, alignment of the at least two devices is achieved when the re-calculated TOF of a pulse radiating between the at least two acoustic devices is minimized.

These and other aspects, features, and advantages can be appreciated from the accompanying description of certain embodiments of the invention and the accompanying drawing figures and claims.

DETAILED DESCRIPTION OF CERTAIN EMBODIMENTS OF THE INVENTION

Figure 1:
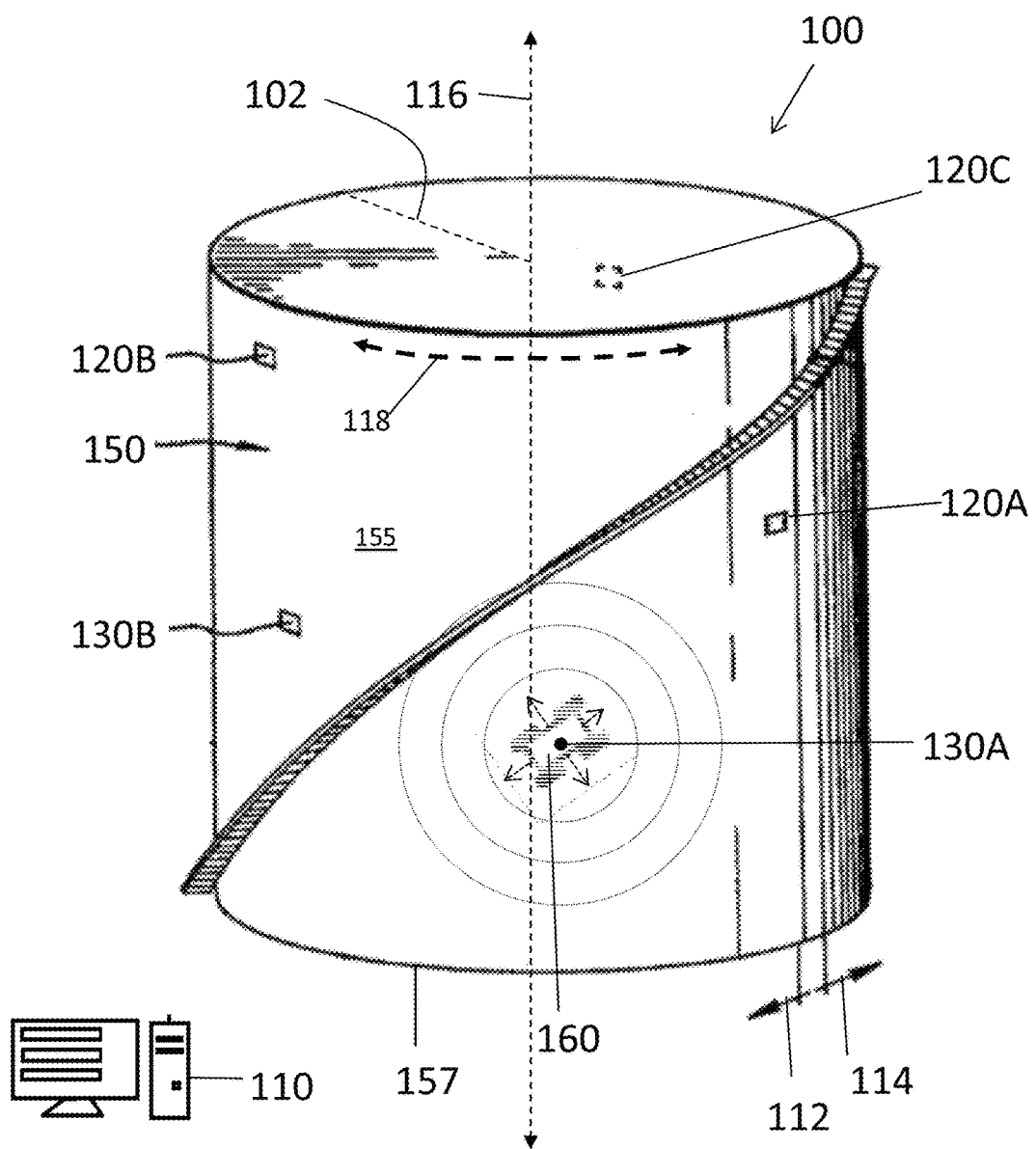
FIG. 1 is a high-level diagram illustrating an exemplary configuration of a system for calibration of the volume of storage containers according to an embodiment of the invention.

By way of overview and introduction, a system and method is disclosed for calibrating the volume of a storage containers. More specifically, the systems and methods disclosed herein are directed to measuring and determining the dimensions of large petroleum storage tanks so as to calculate the volume of such tanks using acoustic or, more generally, mechanical wave-based inspection techniques. Preferably, the systems are configured to perform the calibration from the exterior of the container on-demand during the use of the containers in the field.

Acoustic testing is a non-destructive and non-invasive testing technique based on analyzing the propagation of acoustic waves in the material being tested (e.g., the wall of the container). In the embodiments described herein, the measuring techniques are performed to measure the volume of large storage containers that are typically generally cylindrical in shape and are typically made of steel or other metals and alloys. However, the disclosed techniques and systems can also be applied to calibrate the volume of structures made of other materials such as concrete, composites, natural materials (e.g., wood) or combinations of the foregoing. In addition, the systems and techniques disclosed herein can also be applied to measure the volume of containers having different sizes and shapes as well. For instance, the exemplary embodiments can be used to measure the volume of open or closed vessels, tanks and other such containers or conduits of various sizes.

In some exemplary configurations, the container volume calibration system comprises an array of measurement devices having associated electronic hardware and/or software suitable for controlling their operation. The measurement devices are configured to be attached to the exterior surface(s) of a storage container (e.g. by hand, robot, etc.) thereby defining the array of devices. The measurement devices are configured to take mechanical or acoustic wave-based measurements that enable the determination of the container's volume by a diagnostic computing device that is in communication with the acoustic devices. More specifically, the array of devices includes one or more sensors configured to receive, measure and process signals propagating within or along the wall of the container. The array of devices also includes at least one signal generating element or "transducer" that is configured to generate the signals that propagate along the wall of the container.

The sensors/generating elements (collectively referred to as the "measurement devices") are connected to and controlled using a diagnostic computing device (hereinafter referred to as the controller or control computer), which is configured to determine the time between the generation of an acoustic signal using the sound generating element and the arrival of at least a first acoustic wave at the sensor through the wall of the container (i.e., the "time-of-flight" or "TOF" of the acoustic signals). Ideally, similar TOF information for additional acoustic waves that arrive at one or more of the sensor(s) is measured/collected as well (e.g., the time-of-flight for a second acoustic wave moving around the container in the opposite direction of the first wave). Accordingly, the dimensions of the container wall (e.g., the circumference, volume, height of the container and the like) can be calculated using such geometric information by the controller based on the time between the sound impulse and reception of the radiating soundwaves and based on the speed of sound through the material of the wall. Moreover, the internal volume of the container can be calibrated/measured based on the geometric measurements of the wall and other known properties of the container such as the wall thickness.

In some basic configurations, the system for calibrating the volume of storage containers includes one transducer and one sensor. In more complex configurations the system includes a plurality of sensors placed on the container at multiple levels (i.e., different heights in the vertical direction) and/or placed at different circumferential positions (i.e., spaced apart about the circumference of the container, such as, one device at the 9 o'clock position and another device at the 3 o'clock when viewing the container from a top view). Based on the placement of the sensors relative to one-another, the detected signal information can be used by the control computer 110 to accurately triangulate and validate each of their respective positions and thus the exact dimensions of the container in multiple dimensions. As a result, a two-dimensional map or three dimensional map of the container can be created using principles of geometry by, effectively, "unwrapping" the outer wall of the container.

According to another salient aspect, the disclosed calibration system can be configured to controllably move one or more of the transmitting and sensing devices into position before and/or during the container volume calibration process, for instance using robots that deploy the various measurement devices on the exterior of the container being calibrated. In such embodiments, alignment in a variety of different directions/dimensions can be achieved among the measurement devices to improve calculations of volume of a container.

An exemplary system for calibration of the volume of a storage container 100 is shown in FIG. 1. As shown in FIG. 1, the container volume calibration system 100 is implemented as an "array" of measurement devices that are arranged for measuring the volume of a metallic storage container 150 having a cylindrical shape. As noted above, exemplary embodiments are described in the context of measuring the volume of storage containers (e.g., 150) having a generally cylindrical shape. It can be appreciated that the cylindrical containers are not necessarily exact cylinders as, for example and without limitation, the cylinder's circumference can differ at different heights on the wall, the cylinder can have non uniform curvature of the wall and can have other such variations in geometry.

The term "longitudinal axis" 116 is intended to refer to the central axis of the container. As shown in FIG. 1, the longitudinal axis 116 is a central axis extending between the base of the container (e.g., where the container is anchored or placed on the ground) and the opposing top end of the container. For simplicity, the disclosed embodiments are described under the assumption that the base of the cylindrical container is anchored on flat ground and extends upwards in the longitudinal direction (i.e., in the vertical direction relative to the ground/base of the container). Accordingly, the term "longitudinal direction" 116 is intended to refer to a direction that is parallel to the longitudinal axis. As can be appreciated, given a container assumed to be anchored to the ground, and as you move away from the base, along the longitudinal axis, there is an infinite set of transverse or "latitudinal" planes extending through the cross-section of the container, on which the acoustic devices can be placed against the exterior surface of the container wall.

Two devices are aligned in the "longitudinal direction" (also referred to as being in "longitudinal alignment") when they have respective positions on the surface of the container that fall in the same transverse or latitudinal plane, which is a plane that is perpendicular to the longitudinal axis and bisects the container. In other words, devices that are referred to as being aligned in the "longitudinal direction" have the same height (i.e., latitude), as measured relative to the base of the container along the longitudinal axis (e.g., both devices are 9 feet off the ground as measured from the base in the longitudinal direction but have different respective angular positions).

Because the cylindrical container is a three-dimensional surface, the term "circumferential direction" 118 is intended to refer to one or more angular directions about the circumference of the container and perpendicular to the longitudinal axis 116. In particular, the circumferential direction about the container's circumference includes the counter-clockwise direction 114 and the clockwise direction 112. It can be appreciated that the circumferential direction 118 is a transverse direction, which refers to one or more directions along the surface that are perpendicular to the longitudinal direction, at respective latitudes.

Devices are referred to herein as being aligned in the transverse direction or "circumferential direction," when their respective positions on the surface 155 fall in the same longitudinal plane (i.e. a plane extending through and along the longitudinal axis) and, preferably, the devices are on opposite sides of the container. For instance, two devices located at angular positions +270 degrees and +90, respectively, relative to a 0 degree reference radius 102 (when the cylindrical container 150 is viewed from the top-view) are circumferentially aligned irrespective of their respective latitudes on the surface.

Because the surface of circumferential wall of the container is also be described herein as an "unwrapped" two-dimensional surface, in two dimensional space, the circumferential direction 118 can be referred to as the "horizontal direction" (i.e., perpendicular to the vertical direction and parallel to the ground) or, more generally, the transverse direction.

Although the exemplary systems and methods for measuring container volume are further described herein in the context of a particular practical application, namely, measuring the volume of large oil storage containers having a cylindrical shape and metallic construction, it should be understood that the subject invention is not limited to this exemplary application. For instance, in some implementations, the cylinders can be oriented such that the central axis extends horizontally relative to the ground. The exemplary techniques disclosed herein are similarly applicable to calibrating the volume of containers having other shapes, for instance, spherical tanks, however, it can be appreciated that such alternative container shapes can require a different set of known parameters (e.g., relative placement or distance between measurement devices) in order to calculate the container volume.

As an aside, it should be understood that the foregoing explains one exemplary convention for describing the positioning of devices relative to the container and one-another and describing the various directions in which the devices can be moved and aligned. Other conventions and terminology can be used to describe the positioning and movement of devices without departing from the scope of the disclosed embodiments of the invention, for example, one can generally refer to latitudinal alignment (also circumferential alignment) as two points with the same latitude, while referring to longitudinal alignment as two points with the same longitude (vertical from each other). According to such a convention, for example, moving a transducer in the circumferential/latitudinal direction can cause the transducer to move through and capture distance measurements with all sensors that are circumferentially aligned.

The system 100 includes one or more sensors are configured to be deployed onto the exterior surface of the side wall 155 of the container 150 (e.g. by hand, robot, etc.). As shown in FIG. 1, a plurality of acoustic sensors 120A, 120B and 120C (shown on the opposite side of the container) are arranged on the sidewall to define an array of sensors. In addition, the system 100 includes at least one signal generating unit 130A (hereinafter referred to as a "transducer") that is configured to generate and apply mechanical signals and, more specifically, acoustic signals to the wall of the container that are suitable for detection by the sensors. Additional transducers 130B can also be used in some implementations. Preferably, each transducer (e.g., 130A) generates signals that radiate away from the point of origin and travel along the surface of the wall. The terminology traveling "through the wall" is intended to mean that the signal propagates within the thickness of the wall or along a surface of the wall, as opposed to the signal passing through the entire thickness of the wall and across the internal volume 160 of the container that is bounded by the wall. The signals propagate through the wall in one or more of the directions that the wall extends (e.g., in the circumferential direction 118 about the container's circumference, in the longitudinal direction 116, and/or a combination of the foregoing). In the exemplary implementation of the system 100 on a cylindrical storage container shown in FIG. 1, the signals preferably travel circumferentially about the wall of the container in, generally, a clockwise direction 112 and a counter-clockwise direction 114. However, it can be appreciated that, in some implementations, one or more of the transducers can be configured to transmit signals through the internal volume of the container.

Various types of signals or "waves" can be transmitted and detected using the transducers and sensors. As noted, the signals generally fall into the broad category of mechanical waves and, in the non-limiting exemplary implementations described herein, acoustic waves. In some implementations, the distance measurements can be based on surface waves and/or compression waves moving inside the material itself, as the sensors can be configured to detect one or more different types of waves. Assuming accurate calibration of the speed of the wave in the medium, the particular type of wave that is being measured does not necessarily impact the corresponding distance measurements, so long as the assumed speed of the wave remains consistent.

In some implementations, measurements based on surface waves can be preferable as they move up and down relative to the surface with the steepest amplitude and can be easier to detect. In general, primary waves can travel faster than secondary waves as they move through a medium, and surface waves travel more slowly than secondary waves. Accordingly, in cases where multiple types of waves are detected using a sensor, the difference in time for each wave type to reach the sensor can be used to measure distance more accurately. For instance, the system can be configured to measure the difference between primary-wave and secondary-wave arrival times at a sensor to determine distance, and then triangulate the respective device positions, as further described herein.

As shown in FIG. 1, the sensors and transducer(s) are electrically connected to (connection means not shown) a control computer 110 that is configured to coordinate the operation of the container volume calibration system 100 and the various measurement devices. The control computer 110 is a computing device and/or data processing apparatus capable of communicating with the various devices of system 100, receiving, transmitting and storing electronic information and processing such information so as to measure and calibrate the volume of storage containers, as further described herein. As further described in relation to FIG. 2, the control computer comprises a processor (not shown), which executes one or more software modules in the form of machine implementable code and, in doing so, is configured to control the transmission and reception of signals by the transducer and sensors, respectively. In addition, the software configures the control computer to analyze the signal information, as generated by the transducer and measured by the sensors, and geometrically calculate various dimensions of the container (i.e., the container's geometry). In some implementations, the software can also configure the processor to evaluate structural conditions of the container as well as other operational characteristics of the container (e.g., the volume of the contents within the container, classify the contents, or structural integrity of the container walls, and the like).

More specifically, the control computer is configured to determine the time between the generation of one or more signals or pulses by the transducer 130A and the arrival of at least a first wave traveling through the wall of the container at the one or more sensors. Ideally, similar "time-of-flight" information for additional waves that arrive at the sensor(s) is measured/collected using the control computer 110 and the devices, as well (e.g., the time-of-flight for a second wave moving around the container in the direction opposite to the first wave). Accordingly, the control computer is further configured to calculate the distance traveled by the signals and the dimensions of the container based on the time between the impulse and reception of the waves and further based on a known speed of sound through the material of the wall. As the speed of sound through the wall can vary depending on the material properties of the container wall, in some implementations, the speed of sound can be assumed based on the material. In addition or alternatively, in some implementations, the speed of sound can also be dynamically calculated using the system 100. For instance, two (2) or more acoustic sensors having a known separation can be used to calibrate the speed-of-sound measurement that informs the calibration of the container volume.

Preferably, the array comprises a plurality of sensors disposed at multiple levels on the wall of the storage container (e.g., at different heights as measured in the longitudinal direction 116 from the base of the container 157, which is assumed to be level). In some implementations, sensors and/or impulse generators that are spaced apart a known amount in one or more of the longitudinal 116 and circumferential direction 118 can be applied to the container. For instance, a strip of multiple spaced-apart sensors can be used. As further described herein, utilizing at least two measurement devices that have a known spacing can aid in the calibration of the system 100 and accuracy assurance when using the system 100 to calibrate the volume of the container. Similarly, in some implementations, the sensors can be individually arranged at known heights around the container. As a result, the accuracy and speed of calculations can be improved. Moreover, the controlled placement of multiple sensors at different levels and circumferential positions serves to accurately triangulate and validate the respective positions of the sensors. Thus the exact dimensions of the 2-dimensional map that can be created by 'unwrapping' the outer wall of the container.

In some implementations, one or more of the measurement devices can be attached in a respective position on the exterior of the container so as to provide a long-term or permanent calibration system. However, in some implementations, one or more of the measurement devices can be deployed temporarily such that the system can be used to calibrate different containers on demand. Moreover, in some portable calibration system configurations, the sensors can be deployed using robots, thus eliminating the need for scaffolding when placing the sensors on the container.

Sensors:

The sensors 120A-120C can be any variety of sensors or transceivers that are suitable for being mounted to the external surface of the container, detecting and receiving mechanical wave signals radiating along the wall from the wall of the container and processing such information, as would be understood by those in the art. Preferably, the sensors have very small tips in contact with surface to minimize error in position relative to detection of the wave. The size of the tip can be defined as a function of the necessary accuracy of the system. Various types of sensors can be used, for instance, piezoelectric sensors, wideband acoustic transducer and the like.

For instance, in some implementations, the sensor can be a piezoelectric sensor that is configured to detect one of various mechanical wave types that propagate along the wall, such as, for example and without limitation, primary waves, secondary waves, surface waves, Rayleigh waves, and the like. In implementations in which the sensor is configured to detect multiple different types of waves, it can be further preferable for the sensor and/or the control computer to differentiate between different types of waves received at the sensor. Moreover, in some implementations, the sensors can be configured to measure lateral or radial movement of the surface according to a variety of methods (for example, stress/strain, pressure, vibration, and the like), as would be understood by those in the art.

Preferably, the sensors are in electronic communication with the control computer such that the control computer can control operation of the sensors and such that the sensors can provide received signal data to the control computer for further processing.

Signal Generators:

As noted above, the signal generating device (e.g., transducer 130) can be any variety of transducer or transceivers that are suitable for applying mechanical and/or acoustic signals to the wall of the container such that they travel through or along the wall of the container about the circumference of the container, as would be understood by those in the art.

In a more basic implementation, the transducer can be an electro-mechanical device configured to controllably strike the surface of the container with a hard object so as to generate a mechanical pulse or wave. In addition or alternatively, the impulse generator can be an acoustic transducer. In the following description, the term "acoustic" is to be construed broadly to include mechanical waves and acoustic signals, for example, acoustic signals in a frequency range of 100 Hz to 50 MHz, more optionally in the ultrasonic acoustic radiation range. However, in some implementations, signals having lower frequencies can be used and can improve accuracy by, for example, minimizing unwanted reflections of the signal and facilitating differentiation of signals by allowing for easier detection of the particular shape of the signal.

Each transducer can be configured to generate a signal comprising at least one pulse that travels along the wall of the container toward a sensor(s) configured to detect the signals. Accordingly, by generating at least one mechanical pulse using transducer(s) at respective locations, a corresponding distance traveled by the individual pulses can be measured. Although each transducer can be configured to transmit a signal comprising individual impulses/pulses, the transducer can also be configured to generate waves, for instance, a stream of pulses having a particular frequency, shape, wavelength amplitude and the like.

The transducer can be configured to apply signals to the wall of the container such that the signal radiates away from the point of origin of the pulse. Preferably, the transducer is configured to use the wall of the container as a waveguide so as to guide the propagation of the signal from the point of origin along the surface of the wall. In some configurations the transducer is configured to introduce the signal such that it propagates in one or more defined directions such that the signals propagate around the circumference of the container in a controlled manner.

Preferably, the transducer is in electronic communication with the control computer such that the control computer can control operation of the transducer. In some implementations, the transducer can be configured to introduce signals having certain properties, namely, specific frequencies or specific ranges of frequencies. The properties of the signals can be defined by the specific hardware configuration of the transducer and, in addition or alternatively, controlled using the control computer.

More specifically, preferably, the waves do not move (i.e., echo) between one surface of the wall and the other (e.g., bounce radially between surfaces), as this can artificially increase the distance travelled by the wave and create noise as some portion of the wave got behind the leading edge. Accordingly, in some implementations, the frequency of the signal could be calibrated to minimize reflections within the material. For instance, using a low frequency signals can lead to more accurate results, as the thickness of the container walls might otherwise allow the signal to bounce within the wall. By way of further example, signals having a wavelength that is longer than the thickness of the wall can be used and can keep the signal from echoing within the thickness of the wall. Thus, if the frequency is sufficiently low (e.g., such that one (1) wavelength cannot fit into the thickness of the wall) echoing in the wall should be minimized, and thus the propagation of the signal should be more consistent along the surface.

In some applications, the soundwaves might interfere with each other at certain frequencies. In addition, higher frequencies can increase the sharpness of the signal and assist accurate detection, however, at the cost of potentially losing amplitude and/or echoing of the signal as noted above. Accordingly, the control computer and transducer can be configured to modulate the frequency of impulses so as to allow for more accurate detection of the leading edge of each impulse as it reaches the sensor in view of constraints relating to the specific application such as container wall thickness, circumference, etc. Other suitable signal characteristics can also be selected or modulated in the methods and systems herein, for instance, the amplitude and wavelength of the pulses can be modulated or defined.

Robotic Deployment:

As previously noted, in some configurations, the system 100 can include one or more robots that are configured to autonomously and semi-autonomously deploy one or more of the measurement devices on the container being calibrated in a temporary fashion. In the exemplary configuration shown in FIG. 1, the acoustic transducer 130A is deployed using a robot 160. In some configurations, the robot can deploy a measurement device by attaching the device to the container at respective locations. Accordingly, the robot can deploy multiple different measurement devices. In other configurations, a measurement device can be mounted to a robot such that deployment comprises moving the robot into position and which places the device in communication with the wall 155 and which can thereafter move to another position, as necessary. In such an arrangement, the robot can reposition itself and optionally move the device into engagement with the container under programmatic control of code implemented by the system.

As would be understood by those in the art of robotics, each robot 160 is a mobile robotic device that includes a body and a motion system for moving the robot during operation. The robot can be powered by, for example, solar cells, batteries, or any other suitable power source. The robot can include functional hardware components specifically designed to facilitate performing operational tasks, for instance, sensors for detecting height, position, orientation of the robot, and the like. The robot hardware can also include on-board acoustic sensors and transducers used in the container volume calibration processes and, in addition or alternatively, components suitable for transporting and deploying measurement devices configured to operate in a stand-alone fashion. The robot can include electronic circuitry within the body that includes a memory and/or computer readable storage medium which are configured to store information relating to the operation of the robot such as configuration settings and one or more control programs that facilitate the performance of the container volume calibration operations.

According to a salient aspect, in some embodiments, the system 100 can be configured to controllably deploy the measurement devices into position (e.g. by hand or using the robots) before and/or during implementation of the container volume calibration process so as to accurately measure the container volume in an automated fashion. More specifically, a robot-based deployment solution can be implemented to automatically execute more complex calibration procedures with a high degree of precision thereby improving the accuracy of the container calibration results by virtue capturing mechanical or acoustic wave-based measurements for any number of different sensor and/or transducer placement schemes. For example, robots can be controlled by the control computer 110 to systematically move the sensors and/or the transducer into different positions on the container wall (e.g., various heights, relative positions, absolute positions etc.) such that acoustic measurements can be taken for each arrangement of devices and the measurements can thereafter be analyzed individually and in combination to generate a detailed map of the container's shape and, more particularly, the container volume.

Figure 2:
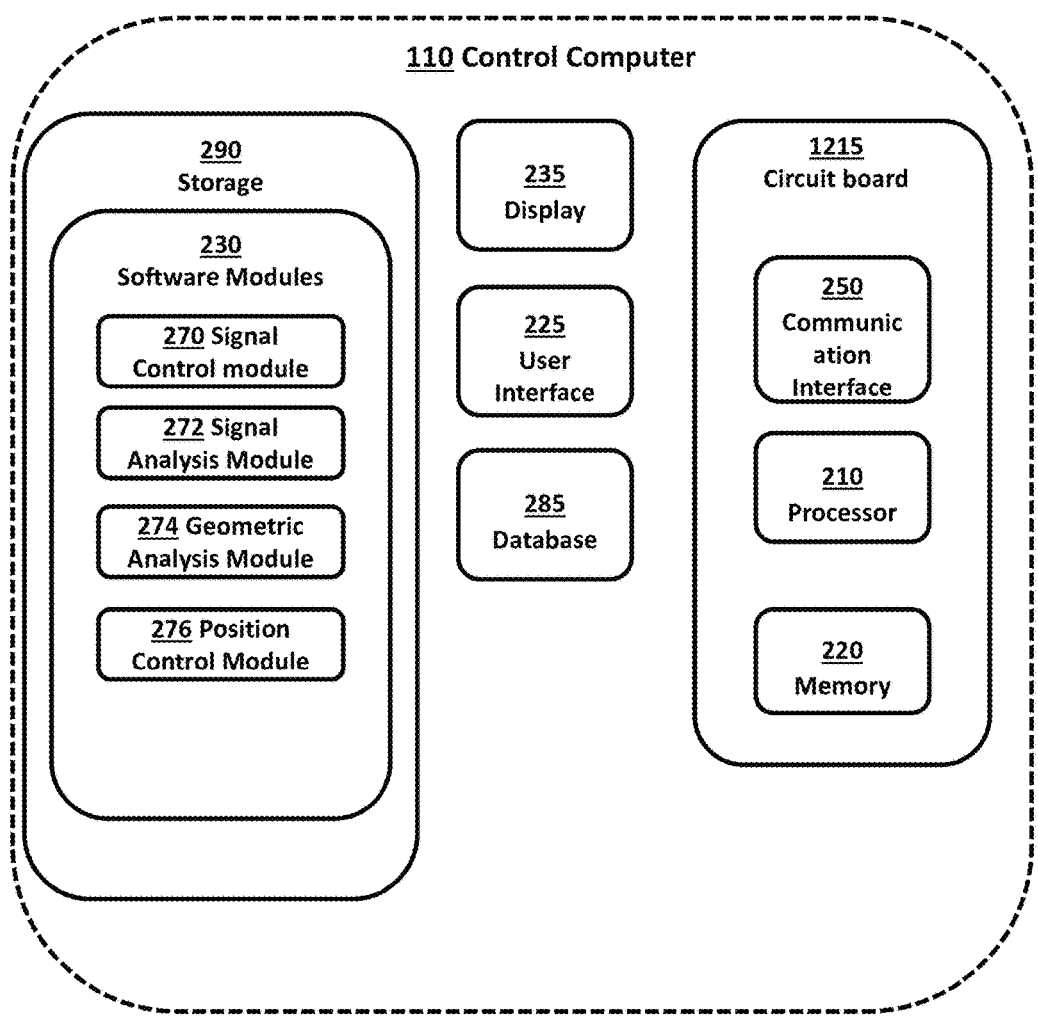
FIG. 2 is a block diagram illustrating an exemplary configuration of a control computer according to an embodiment of the present invention.

The exemplary control computer 110 is further described in reference to FIG. 2. As shown, the control computer 110 can be arranged with various hardware and software components that serve to enable operation of the system 100, including a circuit board 215, a processor 210, a memory 220, a display 235, a user interface 225, a communication interface 250 and a computer readable storage medium 290.

The processor 210 serves to execute software instructions that can be stored in the storage 290 and loaded into the memory 220. The processor 210 can be a number of processors, a multi-processor core, or some other type of processor, depending on the particular implementation. The display can be displayed on a touchscreen or other display operatively coupled to an input device (not shown).

Preferably, the memory 220 and/or the storage 290 are accessible by the processor 210, thereby enabling the processor 210 to receive and execute instructions stored on the memory 220 and/or on the storage 290. The memory 220 can be, for example, a random access memory (RAM) or any other suitable volatile or non-volatile computer readable storage medium. In addition, the memory 220 can be fixed or removable. The storage 290 can take various forms, depending on the particular implementation. For example, the storage 290 can contain one or more components or devices such as a hard drive, a flash memory, a rewritable optical disk, a rewritable magnetic tape, or some combination of the above. The storage 290 also can be fixed or removable, local storage or remote storage such as cloud based data storage systems.

One or more software modules 230 are encoded in the storage 290 and/or in the memory 220. The software modules 230 can comprise one or more software programs or applications having computer program code, a script, or a set of interpretable instructions executed in the processor 210. Such computer program code or instructions for carrying out operations and implementing aspects of the systems and methods disclosed herein can be written in any combination of one or more programming languages or scripts. The program code can execute entirely on the control computer 110, as a stand-alone software package, partly on the control computer and partly on a remote computer/device (e.g., sensors, transducers and/or robots) or entirely on such remote computers/devices. In the latter scenario, the remote computer systems can be connected to control computer 110 through any type of electronic data connection or network, including a local area network (LAN) or a wide area network (WAN), or the connection can be made through an external computer (for example, through the Internet using an Internet Service Provider).

Preferably, included among the software modules 230 is a signal control module 270, a signal analysis module 272, a geometric analysis module 274, a position control module 276 that are executed by processor 210. During execution of the software modules 230, the processor 210 is configured to perform various operations relating to the calibration of storage containers, as will be described in greater detail below.

It can also be said that the program code of the software modules 230 and one or more of the non-transitory computer readable storage devices (such as the memory 220 and/or the storage 290) form a computer program product that can be manufactured and/or distributed in accordance with the present disclosure, as is known to those of ordinary skill in the art.

It should be understood that in some illustrative embodiments, one or more of the software modules 230 can be downloaded over a network to the storage 290 from another device or system via communication interface 250 for use within the system for configuring field robots 100.

In addition, it should be noted that other information and/or data relevant to the operation of the present systems and methods can also be stored on the storage 290, for instance various control programs used in the operation of the measurement devices (e.g., sensors and transducers) and/or the robots during use.

A database 285 can also be stored on the storage 290. Database 285 can contain and/or maintain various data items and elements that are utilized throughout the various operations of the system 100. The information stored in database 185 can include, but is not limited to, software and information for coordinating the operation of the measurement devices, software and information for coordinating the movement of robots while deploying measurement devices into their respective positions during container calibration, known characteristics of the containers that are used to perform the acoustic measurements and calculate container dimensions (e.g., container wall thickness, container wall material composition, container contents, container height, rough dimensions of the container). It should be noted that although database 285 is depicted as being configured locally to the storage of the control computer 110, in certain implementations, database 285 and/or various of the data elements stored therein can be located remotely and connected to the control computer 110 through a network in a manner known to those of ordinary skill in the art.

A communication interface 250 is also operatively connected to the processor 210 and can be any interface that enables communication between the control computer 110 and external devices, machines and/or elements such as the transducer, sensors and any robots used in connection with the calibration operations. Preferably, the communication interface 250 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the control computer 110 to other computing devices and/or communication networks, such as private networks and the Internet. Such connections can include a wired connection or a wireless connection (e.g., using the IEEE 802.11 standard) though it should be understood that communication interface 250 can be practically any interface that enables communication to/from the control computer.

Figure 3:
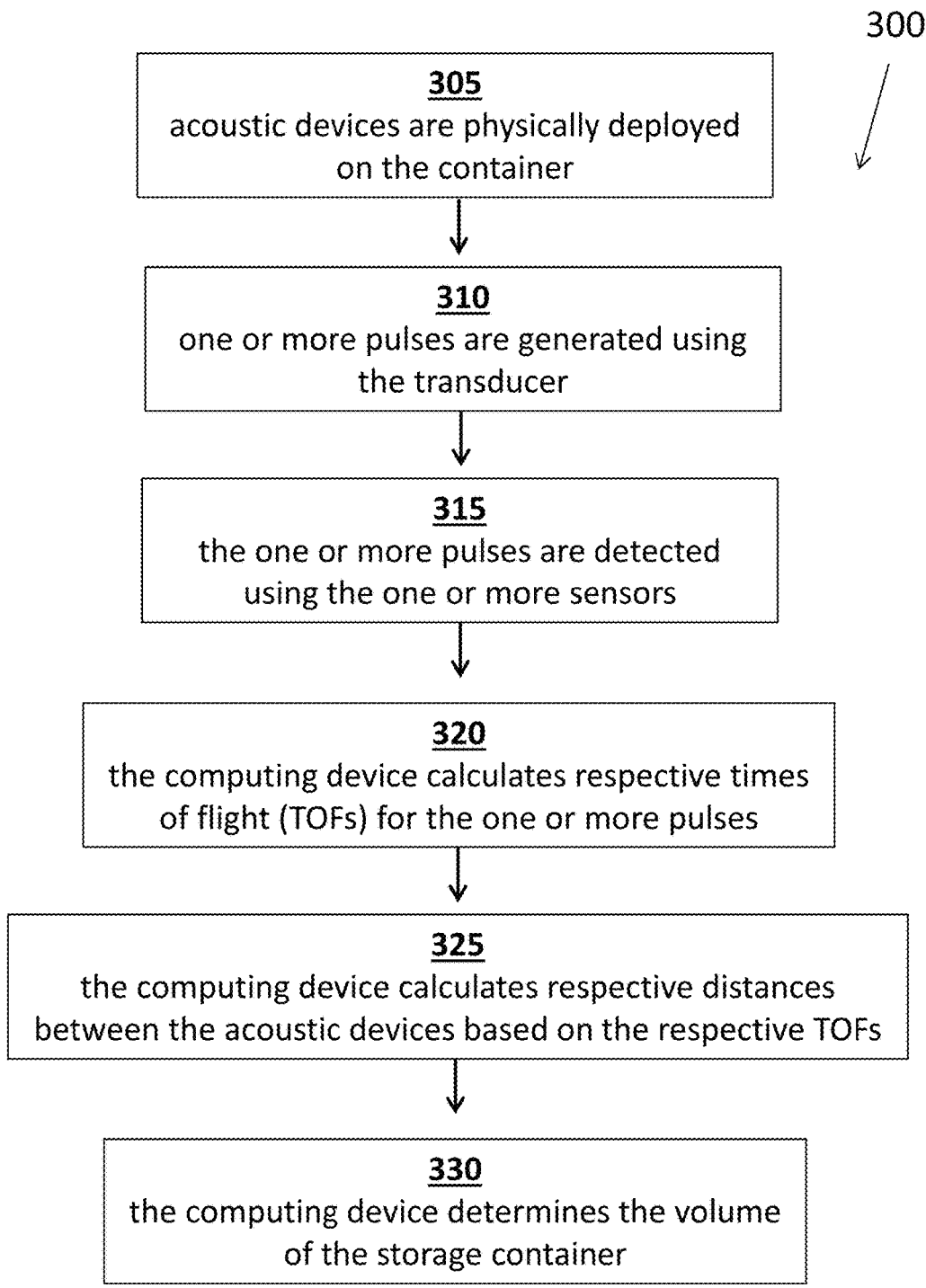
FIG. 3 is a flow diagram showing a routine that illustrates the systems and methods for calibration of the volume of storage containers according to an embodiment of the present invention.

The operation of the system for calibrating container volume 100 and the various elements and components described above will be further appreciated with reference to FIG. 3. FIG. 3 is a high-level flow diagram illustrating elements of a routine 300 for calibrating the volume of a storage container according to embodiments of the invention. The method of FIG. 3 is discussed in reference to an exemplary practical implementation of the system 100 illustrated in FIGS. 4A-4D, however, it should be understood that routine 300 can similarly be applied in connection with the exemplary calibration system configurations and processes described in the context of FIGS. 5A-9.

The routine 300 begins at step 305, when the acoustic devices are physically deployed on the container at respective positions. More specifically, one or more acoustic sensors and one or more acoustic transducers can be deployed into respective positions on an exterior surface of the wall of the container by hand or using robots. Preferably, the one or more sensors are acoustically coupled to the wall such that they are configured to detect acoustic signals that are traveling along the surface. The transducer is acoustically coupled to the surface and, in one embodiment, is configured generate one or more pulses that are applied to the wall at a point of origin thereby causing soundwaves to radiate away from the transducer's position along the surface. The "position" of an acoustic device should be understood as referring to the location (e.g., a point or area) on the surface of the container where the device transmits and/or receives the acoustic signals. Moreover, preferably, the acoustic sensors have tips in contact with surface that are of a suitable size to achieve the required accuracy in the measurement and, thus, minimize error in detection of the soundwave. For instance, the sensor tip can have a smaller diameter than the required accuracy tolerance for the distance-based measurements.

Figure 4A:
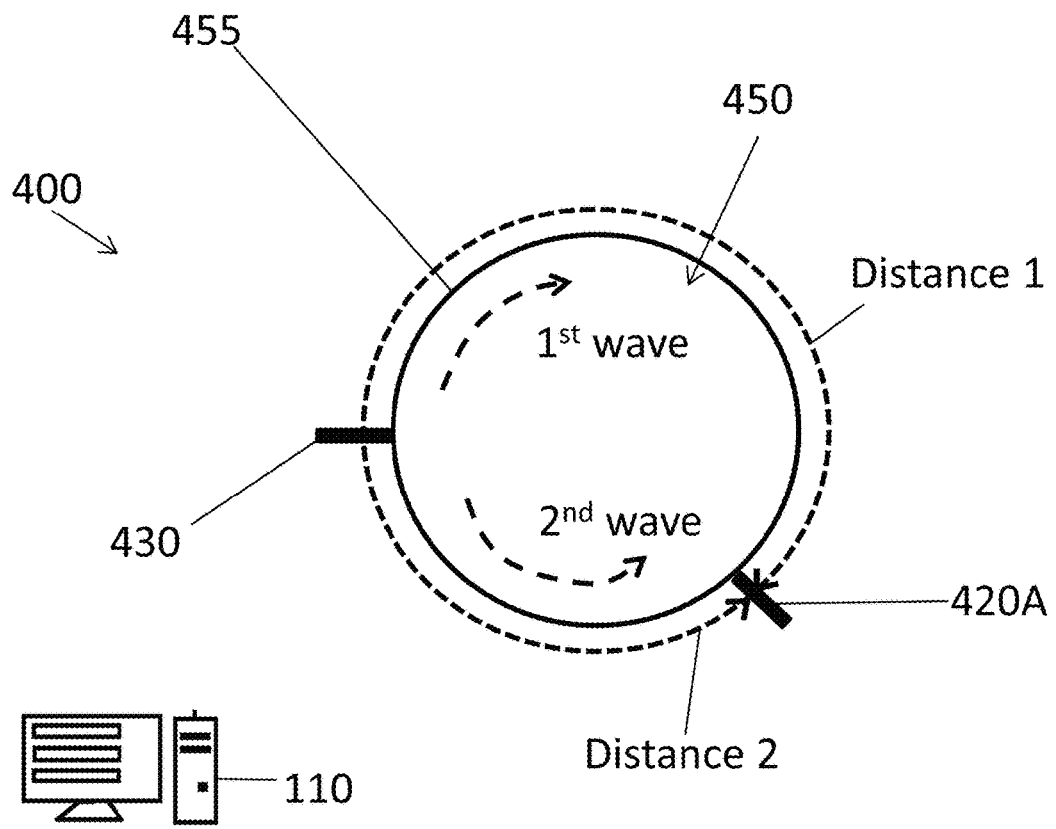
FIG. 4A is a simplified top view of an exemplary container volume calibration system according to an embodiment of the present invention.
Figure 4B:
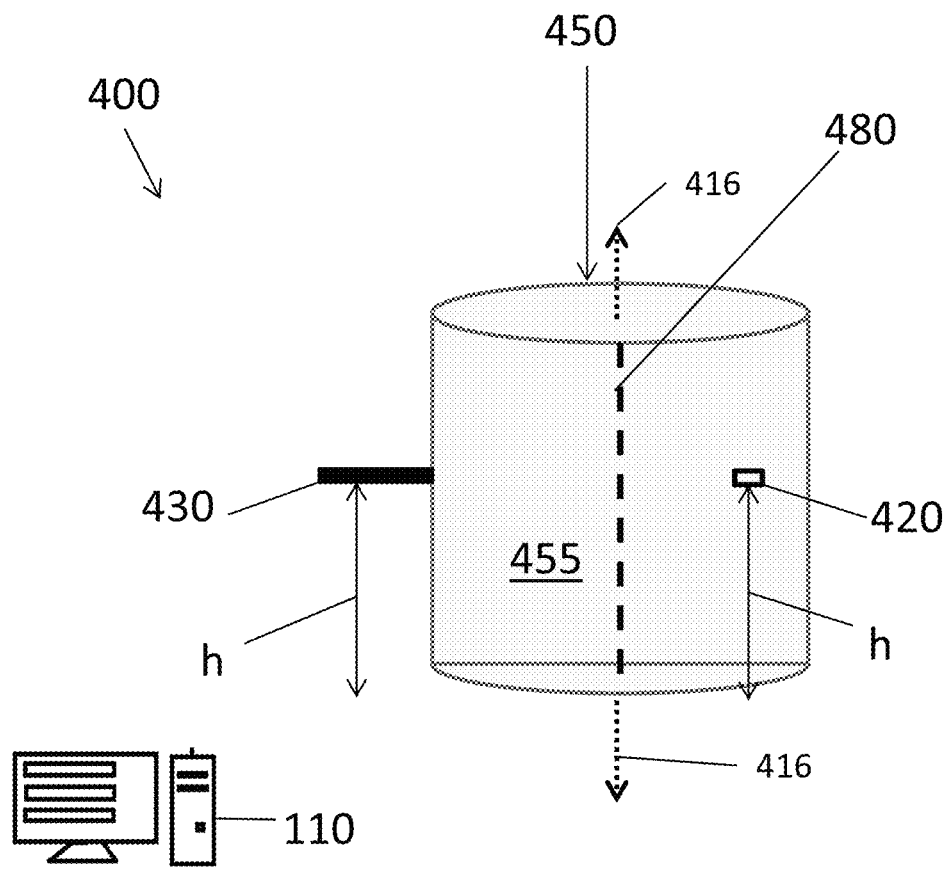
FIG. 4B, is a side-view of the exemplary container volume calibration system of FIG. 4A.

FIG. 4A is a simplified top view of an exemplary container volume calibration system 400 that includes acoustic devices, namely, a transducer 430 and a first sensor 420A disposed on the exterior surface of a wall 455 of a cylindrical container 450. Also illustrated is a control computer 110 in communication with the acoustic devices (430 and 420A) and configured to coordinate the operation thereof. As shown in FIG. 4B, which is a side-view of the system 400 deployed on the container 450, the transducer 430 and the first sensor 420A are positioned at the same height (h) on the wall of the container (measured in the longitudinal direction 416), such that they are aligned in the longitudinal direction (i.e., as explained above, at the same latitude). Assuming that the transducer and the sensor are provided at the same latitude (i.e., such that acoustic signals can travel from the transducer to the sensor along the most direct/shortest circumferential path there-between), the following exemplary steps of routine 300 can be performed using the system 400 to calculate the circumference of the container at the given latitude of the acoustic devices. It should be understood that additional sensors 420 (e.g., 420B, 420C, etc.) can be utilized in any given arrangement as discussed in connection with FIGS. 5A-9.

Figure 4C:
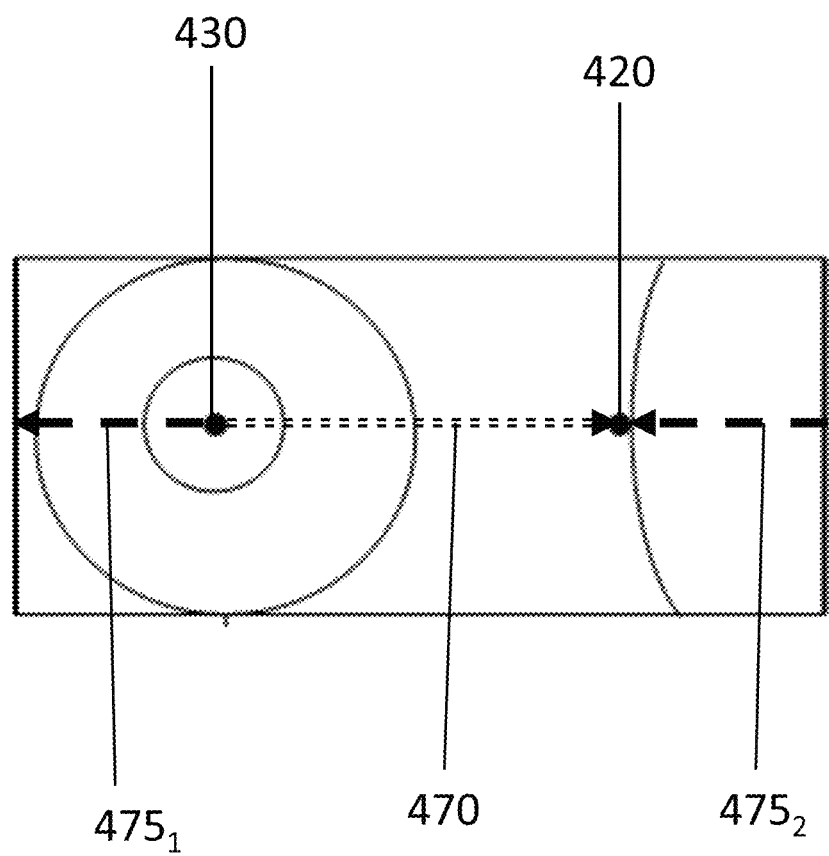
FIG. 4C depicts a flattened two-dimensional view of the exemplary container volume calibration system of FIG. 4A.

At step 310, one or more pulses are generated using the transducer. In a practical application, the control computer 110, which is configured by executing one or more of the software modules using, for example and without limitation, the signal control module 270, can cause the transducer 430 to generate a pulse. The control computer can also record various parameters relating to the pulse including, for example, an impulse time. Other parameters can include the characteristics of the pulse such as intensity, frequency and the like. Preferably, the pulse is applied to the wall 455 from the respective location of the transducer and radiates outward from the point of origin along the surface of the wall. In particular, a first component of the pulse (the "first soundwave") travels along the surface in a clockwise direction and a second component of the soundwave (the "second soundwave") travels along the surface of the container in a counter-clockwise direction. FIG. 4C depicts a flattened two-dimensional view of the container wall from the perspective of the interior surface of the wall (as if the wall were cut along imaginary dividing line 480 shown in FIGS. 4A and 4B and unwrapped/flattened). FIG. 4C illustrates the soundwave radiating from the origin of the pulse (i.e., the location of the transducer 430). Effectively, as shown in FIG. 4C, the first soundwave travels from the point of origin to the position of the sensor 420A along a first path 470 and the second soundwave travels along a second path 475.

Returning now to routine 300, at step 315, the one or more pulses are detected using the one or more sensors. It can be appreciated that, given the particular relative placement of acoustic devices illustrated in FIG. 4A-4D, the first soundwave travels a longer distance ("distance 1") before reaching the sensor 420A than the second soundwave ("distance 2"). As a result, the arrival of the second soundwave is detected by the sensor before the arrival of the first soundwave. In addition, at step 315, information relating to the detected soundwaves can be measured using the sensor and recorded by the control computer 110 for further processing. Preferably, this information includes a particular time that the sensor detects the arrival of the soundwaves, respectively. In addition, the information measured and recorded for further analysis can include characteristics of the soundwaves such as intensity, frequency and the like. For instance, the characteristics of the detected soundwaves can be analyzed using the control computer to distinguish pulses and, in some implementations, to determine various operational conditions of the container.

Then at step 320, the control computer 110 calculates respective times of flight (TOFs) for the one or more pulses based on the impulse time and respective detection times for the one or more pulses. Each respective TOF represents the elapsed time for a pulse to travel between two of the acoustic devices and is a function of the distance traveled by the pulse, for instance, the time to travel from the transducer's location to the point where it was first detected by a particular sensor.

More specifically, in the exemplary implementation shown in FIGS. 4A-4D, the control computer 110, which is configured by executing one or more of the software modules 130 including, for example and without limitation, the signal analysis module 272, can calculate a TOF for the first and second soundwaves traveling along the first and second paths, respectively, based on the elapsed time between the impulse time and respective times that the first and second soundwaves were detected by the first sensor 420A. Moreover, the control computer can extrapolate the total time it would take the pulse to travel around the entire surface of the container by summing the TOFs calculated for the first and second waves.

Figure 4D:
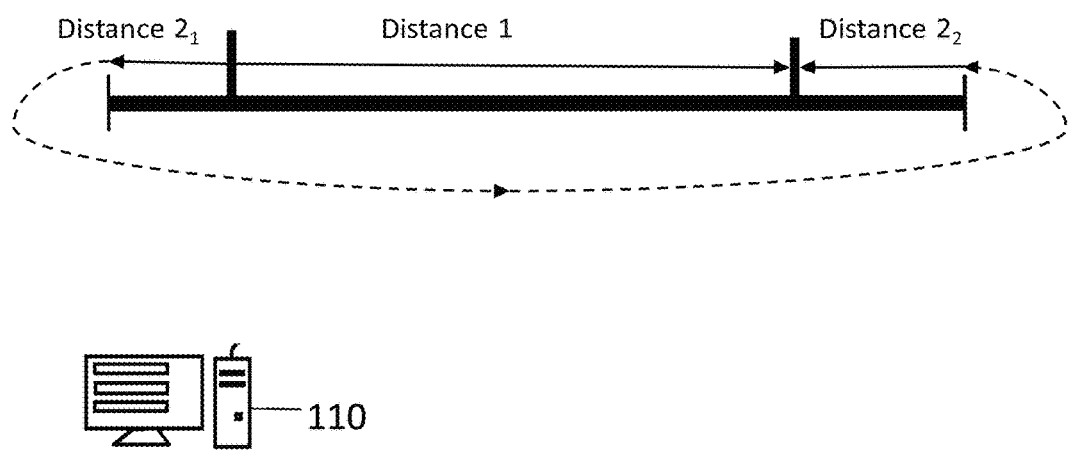
FIG. 4D is a conceptual linear graphical depiction of acoustic signal paths in the exemplary container volume calibration system of FIG. 4A.

At step 325 the control computer 110 calculates respective distances between the acoustic devices based on the respective TOFs and a speed of sound through the wall. More specifically, the control computer, which is configured by executing one or more of the software modules 130 including, for example and without limitation, the geometric analysis module 274, can be configured to calculate the distance traveled by the first and second soundwaves along their respective paths as a function of the calculated TOF and the speed of sound through the material of the container. For instance, distance generally can be calculated according to the equation (distance=TOF*Speed of sound through material). Similarly, assuming that the transducer and the sensor are aligned in the longitudinal direction 418, the circumference of the container can be calculated according to the equation (circumference=(TOF soundwave 1+TOF soundwave 2)*Speed of sound through material). An "unwrapped" linear graphical depiction of the distance traveled by the first and second soundwaves along their respective paths (i.e., the circumferential distance traveled by the pulse) is illustrated in FIG. 4D.

At step 330, the control computer determines the volume of the storage container as a function of the distances calculated at step 325. More specifically, in the example shown in FIGS. 4A-4C, the volume can be calculated based on the acoustically measured circumference of the container and a known height of the container (assuming that circumference does not vary with height).

Although the foregoing steps for calculating the circumference of the container are based on the assumption that the transducer 430 and first sensor 420A are in longitudinal alignment (e.g., at the same height on the container), TOF-based distance measurements between acoustic devices that are not so aligned (e.g., are located at different latitudes) can be similarly used to calculate the dimensions of the container, provided that the relative position of at least two of the acoustic devices is known (e.g., a distance between the at least two devices in one or more of the transverse or longitudinal directions).

The remaining figures and corresponding discussion further illustrate various configurations and concepts of the container volume calibration system 100 in accordance with one or more of the disclosed embodiments of the invention.

Figure 5A:
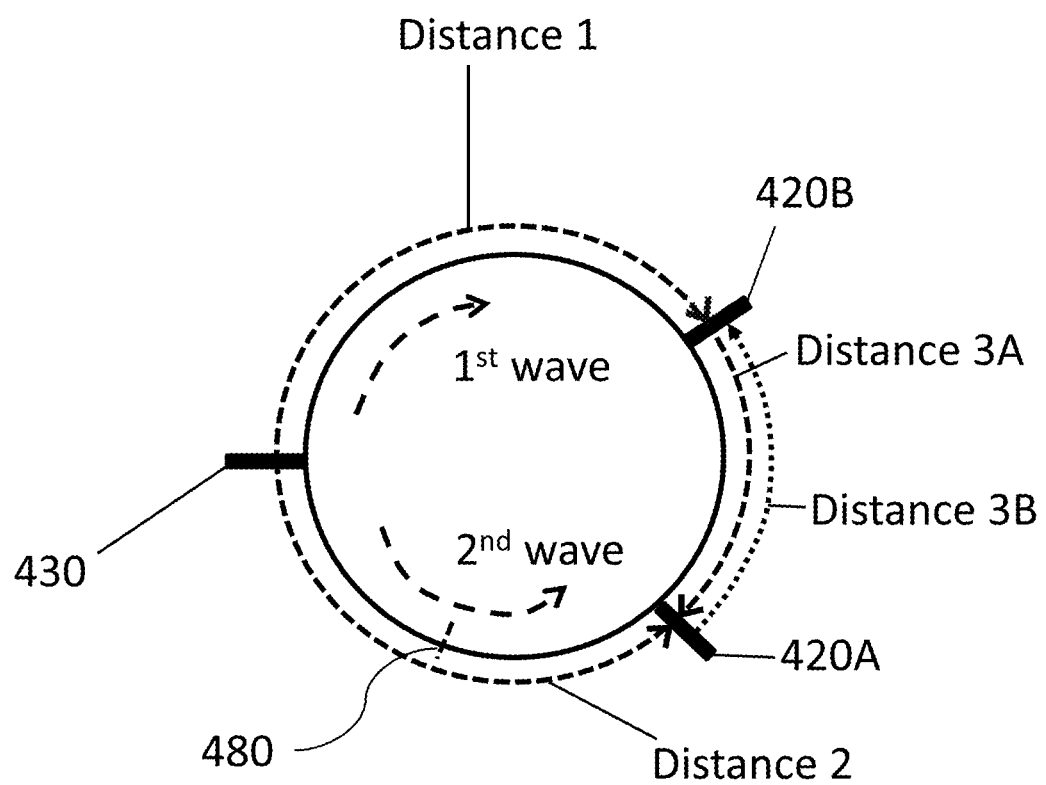
FIG. 5A is a simplified top view of an exemplary container volume calibration system according to an embodiment of the present invention.

FIG. 5A is a top-down view of the system 400 shown in FIG. 4A, but modified to include a second sensor 420B. Although not shown in FIG. 5A, the second sensor 420B is positioned on the same latitude as the first sensor 420A. Accordingly, during operation, the first sensor 420A and second sensor 420B are configured to detect a time that soundwaves from the pulse traveling in the clockwise direction and counter clockwise direction, respectively, are detected.

In some implementations, the control computer 110 can be configured distinguish between detection times that correspond to the first and second soundwaves based on generally known locations of the first and second sensor relative to the transducer. Such general position information can be determined, for example, using GPS or altitude sensors provided on the acoustic devices or measured during deployment, say, by a robot deploying the sensors or a worker manually placing the devices onto the container. For instance, based on an understanding that the first sensor is placed approximately at the five (5) o'clock position (when looking at the container's circumference from a top view) and the second sensor 420B is placed at the 2 o'clock position and the transducer is at the nine (9) o'clock position, the control computer 110 can determine that the first instance of a soundwave detected by the second sensor 420B is the first sound-wave traveling in the clockwise direction and corresponds to a path having a first distance (i.e., distance 1). The control computer can also determine that the second instance of a soundwave detected by the second sensor 420B corresponds to the second soundwave travelling the greater distance about the container in the counter-clockwise direction (i.e., along the path comprising distance 2+distance 3B, as illustrated in FIG. 5A). A similar determination can be made using the acoustic signals detected using the first sensor 420A.

The use of the multiple sensors (i.e., sensors 420A and 420B) can further increase the accuracy of the calibration. In particular, the respective detection times for the second soundwave (which as noted above is travelling in the counter-clockwise direction) measured using the first sensor 420A and the second sensor 420B can be used to determine the time it took for the second soundwave to travel from the first sensor to the second sensor. The respective detection times that are measured using the sensors 420A and 420B for the first soundwave can be similarly used to determine the TOF for the first soundwave traveling from the second sensor 420B to the first sensor 420A.

Figure 5B:
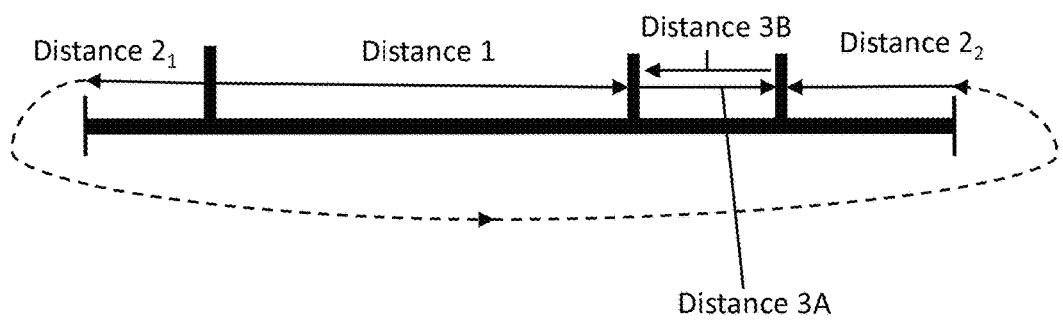
FIG. 5B is a conceptual linear graphical depiction of acoustic signal paths in the exemplary container volume calibration system of FIG. 5A.

As shown in FIG. 5A, the first pulse travels Distance 1 between the transducer and the second sensor 420B, and travels Distance 3A between the first and second acoustic sensors 420A and 420B. Similarly, the second soundwave travels Distance 2 between the transducer and the sensor 420A, and travels Distance 3B between the first and second acoustic sensors 420A and 420B. An "unwrapped" linear graphical depiction of the distances traveled by the first and second soundwaves along their respective paths between the various acoustic devices is illustrated in FIG. 5B.

In some implementations, using the distance between the two sensors can used to calibrate variables used for calculating the container's dimensions. More specifically, if for example the actual Distance 3 is known (e.g., by manual measurement of the distance during deployment), it can be used to ensure accuracy of the speed of sound constant by comparing it to the experimentally determined distance (e.g., Distance 3A and/or Distance 3B). In addition or alternatively, the speed of sound used to calculate the circumference of the container can be adjusted based on one or more of the sensor-based distance measurements. For instance, the speed of sound can be adjusted such that Distance 3A and Distance 3B are closer in value.

Figure 6A:
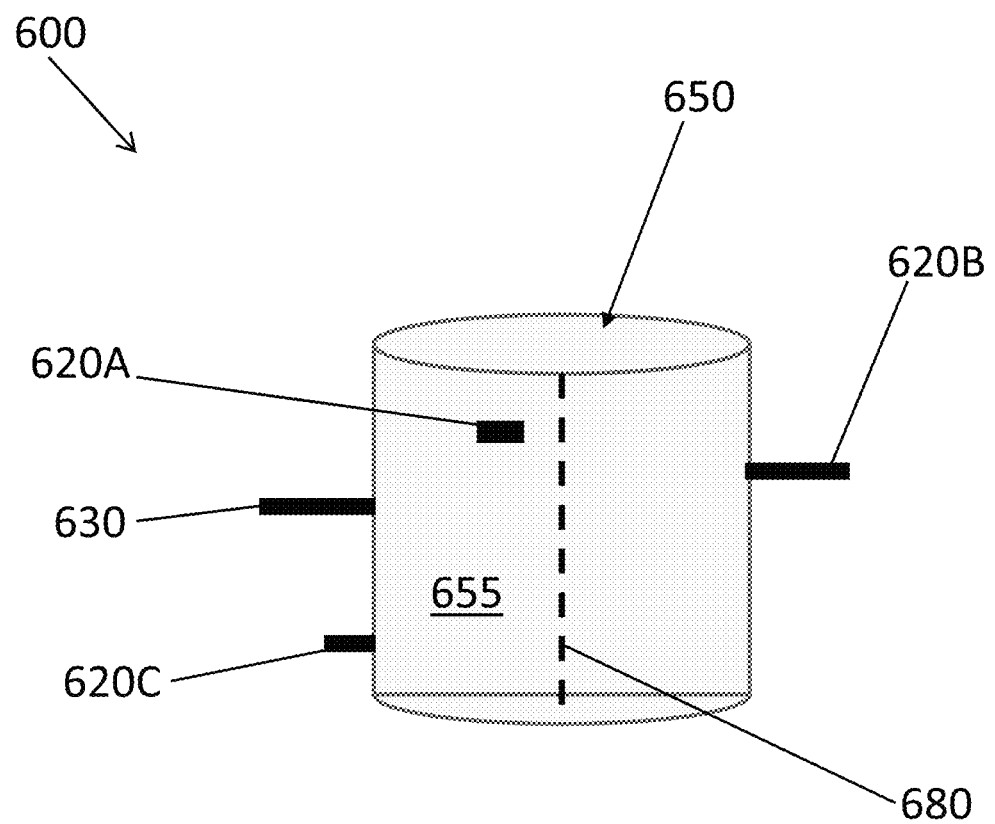
FIG. 6A is a simplified side view of an exemplary container volume calibration system according to an embodiment of the present invention.

FIG. 6A illustrates an exemplary configuration of an container volume calibration system 600 in accordance with one or more of the disclosed embodiments. The system 600 includes a transducer 630 and three sensors 620A, 620B, and 620C placed at respective positions on the surface 655. As shown, the sensors are placed at different respective heights on the container that, in this particular configuration, are also different from the height of the transducer.

Figure 6B:
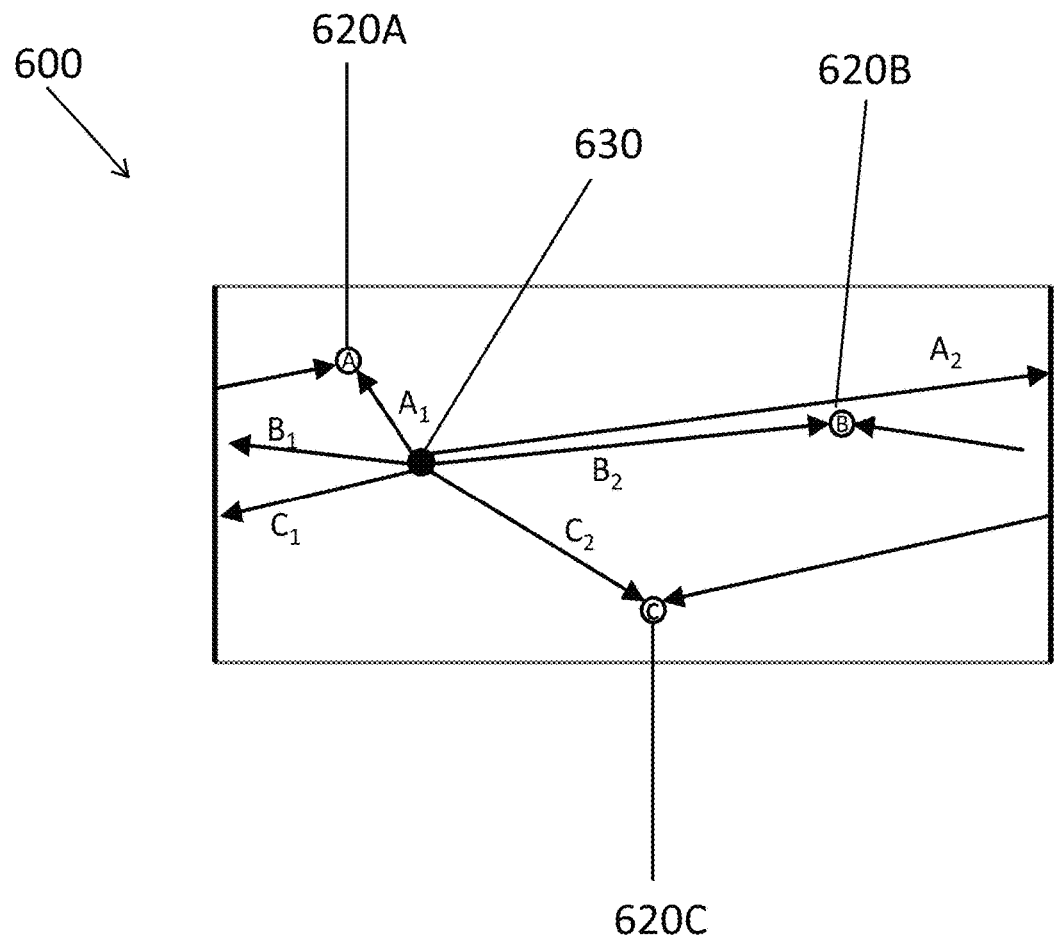
FIG. 6B is a flattened two-dimensional view of the exemplary container volume calibration system of FIG. 6A and conceptually depicts of acoustic signal paths according to an embodiment of the present invention.

FIG. 6B is a simplified two dimensional "unwrapped" view of the container wall 655. FIG. 6B is shown from the perspective of the interior surface of the container wall, as if the wall were cut along imaginary dividing line 680 shown in FIG. 6A and unwrapped or flattened. FIG. 6B also illustrates the paths traveled by a soundwave radiating away from a point of origin (i.e., the location of the transducer 630) towards the sensors, respectively. In particular, the paths of the soundwave traveling generally in the clockwise direction and toward sensors 620A, 620B and 620C are identified as A1, B1, and C1, respectively, and the paths of the soundwave traveling generally in the counter-clockwise direction and toward sensors 620A, 620B and 620C are identified as A2, B2, and C2, respectively.

The TOF of the soundwave travelling along respective paths and the respective distance/length of the paths can be calculated by the control computer (not shown), for instance, according to one or more steps of routine 300. Moreover, assuming that the circumference of the container does not change with the height of the sensors, the dimensions of the container can be mathematically calculated using, for example, the following system of equations:

$$A_{1,y} = A_{2,y}$$

$$A_{1,x} + A_{2,x} = B_{1,x} + B_{2,x}*$$

$$(A_{1,x})^2 + (A_{1,y})^2 = (A_1)^2$$

$$(A_{2,x})^2 + (A_{2,y})^2 = (A_2)^2$$

$$B_{1,y} = B_{2,y}$$

$$B_{1,x}+B_{2,x}=C_{1,x}+C_{2,x}*$$

$$(B_{1,x})^2+(B_{1,y})^2=(B_1)^2$$

$$(B_{2,x})^2+(B_{2,y})^2=(B_2)^2$$

$$C_{1,y}=C_{2,y}$$

$$(C_{1,x})^2+(C_{1,y})^2=(C_1)^2$$

$$(C_{2,x})^2+(C_{2,y})^2=(C_2)^2$$

Calculation using the foregoing solution can require a known position-based relationship between two or more of the acoustic devices. For instance, the known relationship can be a known or independently measured distance between two of the acoustic devices (e.g., sensor 620A and the transducer 630). In some implementations, the known relationship can be a known alignment of at least two acoustic devices on the surface in the longitudinal and/or transverse directions. Calculation of the container's dimensions can also be based on additional assumptions, for instance a constant height of the container, cylindrical shape, constant radius of curvature and the like, as would be understood by those in the art.

Figure 6C:
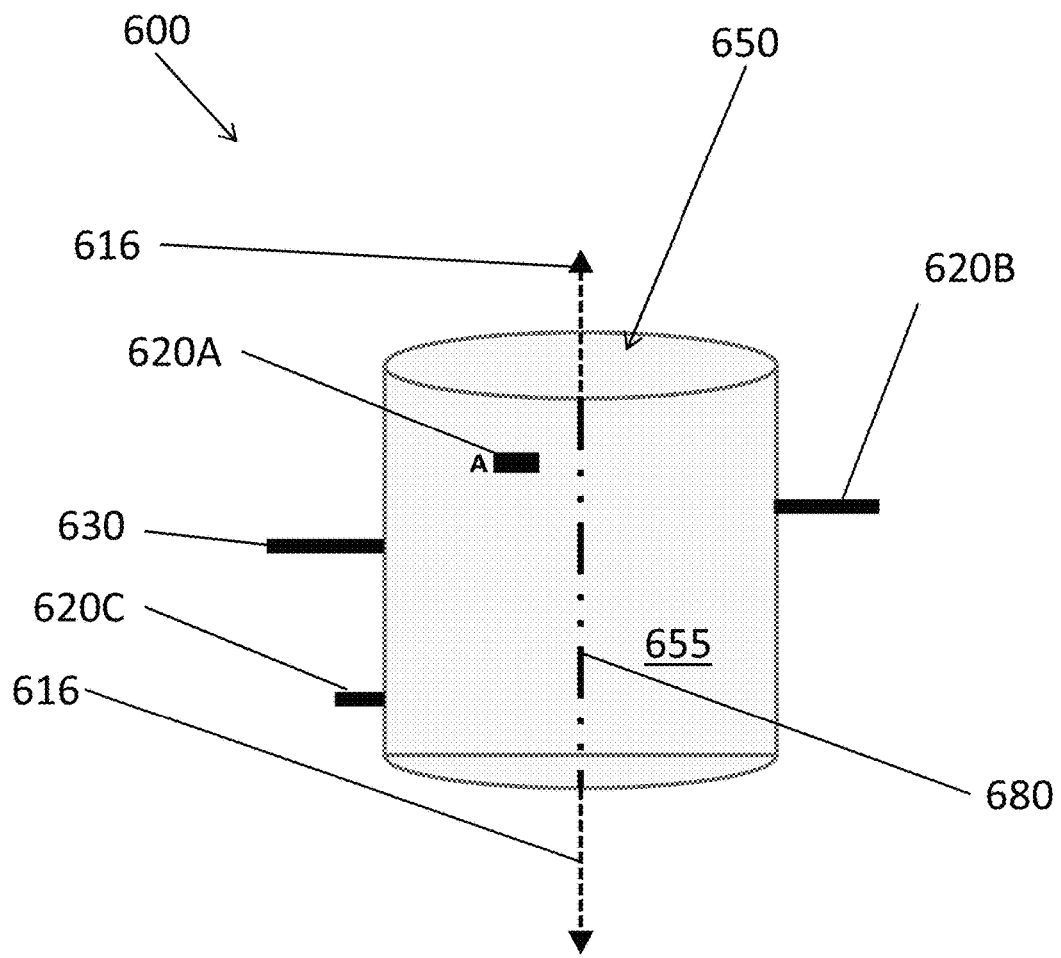
FIG. 6C is a simplified side view of an exemplary container volume calibration system according to an embodiment of the present invention.

FIG. 6C is a side view of the container volume calibration system 600 of FIG. 6A, wherein the acoustic transducer 630 is configured to be moved up or down on the wall in the longitudinal direction. For example, transducer 630 can be mounted to a robot (not shown) that can be controlled using the control computer 110 (not shown) to measurably adjust the position of the transducer 630 during the acoustic container volume calibration process.

As previously noted, positioning the transducer in longitudinal alignment (i.e., at the same longitudinal height on the cylindrical container, which is assumed to be level) with one or more of the acoustic sensors can facilitate accurate calculation of the circumference of the container at the corresponding height of the aligned devices. Accordingly, in one or more exemplary embodiments, the system can be configured to systematically move the transducer 630 longitudinally along the wall 655 of the container 650 (e.g., using a robot) and, for each position that the transducer is level with one or more of the sensors, the circumference of the container can be measured, for instance, according to one or more steps of the previously described routine 300. Thus, in configurations that include multiple sensors located at different heights, the container circumference can be determined at the height of each sensor and, ultimately, the volume of the container can be more accurately calculated in view any height-dependent variations in circumference. It should also be appreciated that the position of the acoustic sensors can similarly be adjusted in the longitudinal direction so as to facilitate measuring of the container's circumference at additional heights.

In accordance with one or more of the disclosed embodiments, the container volume calibration system can be configured to automatically align two or more acoustic devices in one or more directions relative to the circumferential wall of the container. The alignment can be achieved using acoustic-based measurements and, more specifically, based calculated TOFs of acoustic signals between certain devices. In general, verifying that the devices are in alignment can include iteratively adjusting the position of one or more of the acoustic devices on the surface of the container in one or more of the transverse and longitudinal directions and, for each position, repeating the steps of generating, detecting and calculating TOFs until one or more of the re-calculated TOFs indicate that the respective positions of the least two of the acoustic devices are aligned.

More specifically, by way of example and without limitation, the control computer 110, which is configured by executing one or more of the software modules 230, including, for example and without limitation, the position control module 276, can position and re-position the transducer 630 measured amounts in the longitudinal direction along the surface of the container using the robot. Moving the transducer measured amounts in one or more directions on the container surface can be controlled based on position measurements gathered in near-real time, for instance, using one or more sensors that are on-board the robot that are suitable for measuring absolute position or relative position and movement of the robot (e.g., a GPS sensor, accelerometers, altitude sensors, and the like). For each new position of the robot and hence the transducer, the control computer can perform the steps of: generating one or more acoustic pulses using the transducer, detecting the soundwaves traveling along the surface using one or more of the sensors, and calculating TOFs for the one or more pulses. Preferably, when attempting to align the transducer with a particular sensor, say, sensor 620A, TOF is calculated for soundwaves detected by the particular sensor 620A. Because the TOF of soundwaves traveling between the transducer and the particular sensor are directly proportional to distance, alignment is achieved by iteratively moving the transducer until a minimum value of TOF for a pulse traveling there-between is identified. As noted, the control computer can be configured to separate the transducer or other acoustic device from the container, reposition the robot, then place the acoustic device back into engagement with the container at the new location.

Figure 6D:
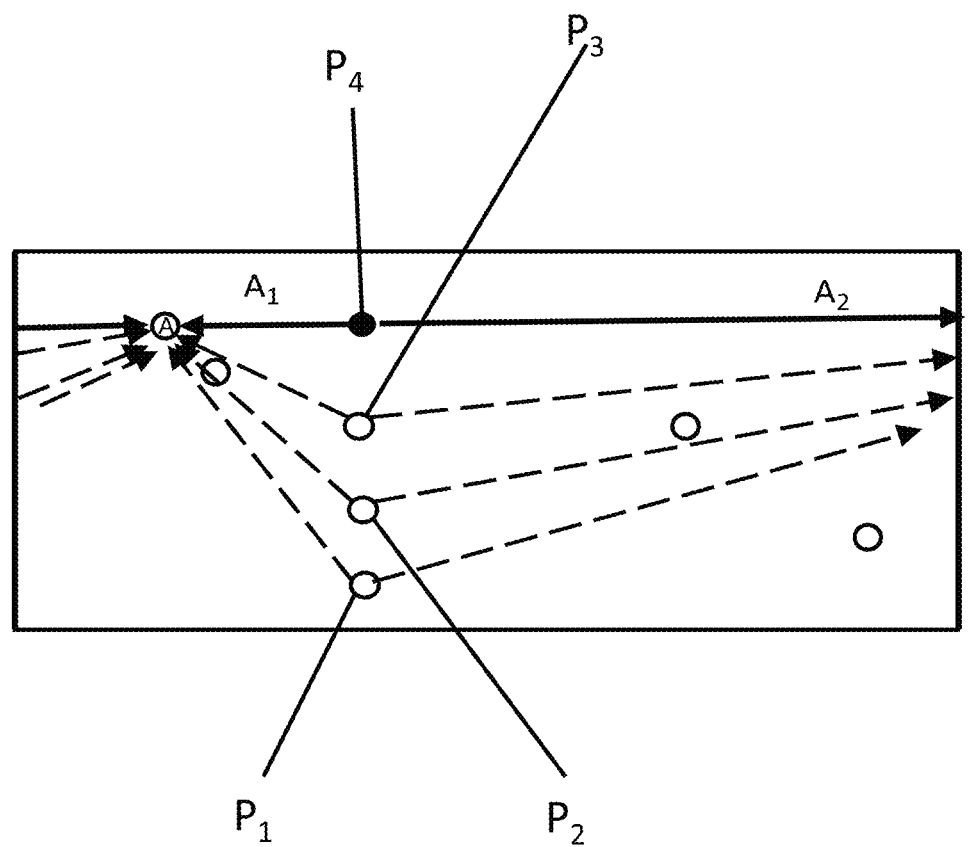
FIG. 6D is a flattened two-dimensional view of the exemplary container volume calibration system of FIG. 6C and conceptually depicts of acoustic signal paths according to an embodiment of the present invention.

FIG. 6D is a two dimensional "unwrapped" view of a section of the container wall 655 from the perspective of the interior surface of the wall (as if the wall were cut along imaginary dividing line 680 shown in FIG. 6A and unwrapped/flattened) throughout the process of aligning the transducer and sensor 620A. FIG. 6D illustrates the multiple positions of the transducer (P1-P4) during the alignment process and, for each transducer position, the corresponding paths traveled by the soundwaves from the transducer to the stationary position "A" of the sensor. As shown in FIG. 6D, the paths A1 and A2 between position P4 of the transducer and sensor position A are the shortest and, thus position P4 can determined to be the transducer position where the transducer is in alignment with the sensor having position A. FIG. 6D further illustrates how a series of vertical transducers (or a moveable transducer mounted on a robot) can provide extra information by creating multiple paths that can lead to a solution for the distance between respective device positions. Specifically, the horizontal line A1 and A2 is important, as it allows for the determination of the container circumference at sensor A, which also provides the placement of that sensor on the tank relative to the robot/line of transducers (in a horizontal direction), thus allowing for a solution to the system of equations.

Figure 6E:
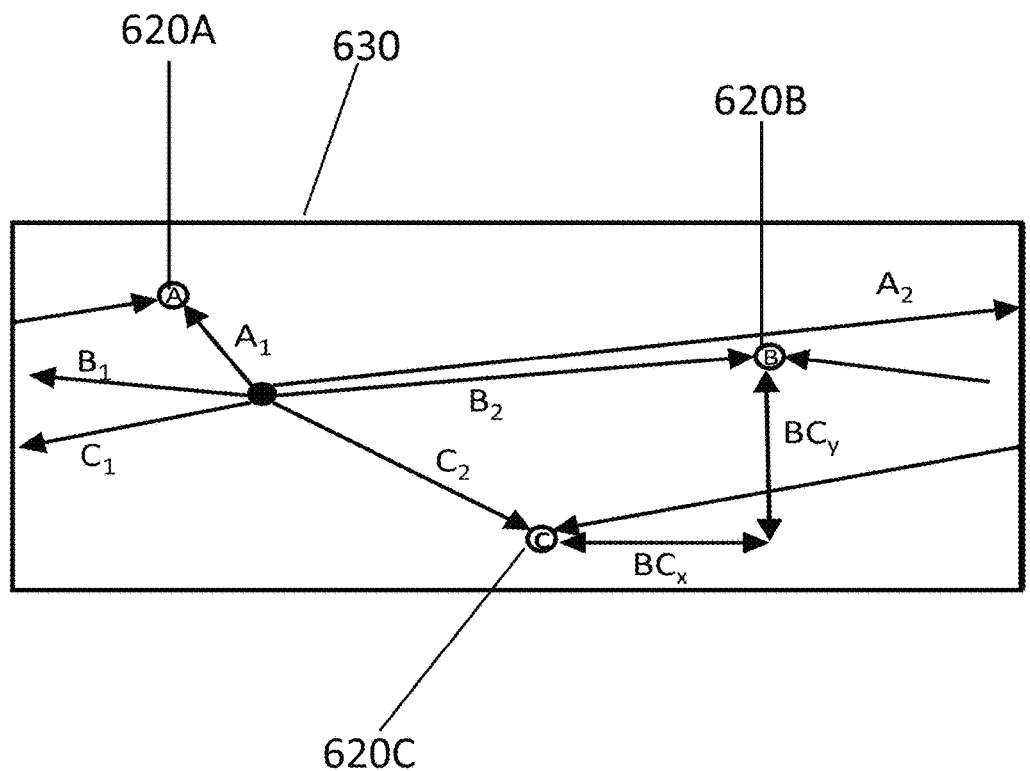
FIG. 6E is a flattened two-dimensional view of the exemplary container volume calibration system of FIG. 6C and conceptually depicts of acoustic signal paths according to an embodiment of the present invention.

FIG. 6E, like FIG. 6B, is a two dimensional "unwrapped" view of the container wall 655 and illustrates the paths traveled by soundwaves radiating away from the transducer 630 towards respective sensors of system 600. Moreover, FIG. 6E illustrates how a known distance between two sensors (or between the transducer and one sensor) aids in solving the system of equations, and/or calibrating for the speed of sound in the material. As can be appreciated, calibration of the container volume calibration system can increase the accuracy of the resulting container volume measurements. In some implementations, calibration can be achieved by measuring distances between sensors in the longitudinal and transverse directions (x, y) along the surface or along a shortest path. For example, as shown in FIG. 6E, if BCx and BCy are measured or known, the following equations are true: By −Cy=BCy and Bx−Cx=BCx. Accordingly, the following set of equations (which were also previously provided):

$$A_{1,y}=A_{2,y}$$

$$A_{1,x}+A_{2,x}=B_{1,x}+B_{2,x}*$$

$$(A_{1,x})^2+(A_{1,y})^2=(A_1)^2$$

$$(A_{2,x})^2+(A_{2,y})^2=(A_2)^2$$

$$B_{1,y}=B_{2,y}$$

$$B_{1,x}+B_{2,x}=C_{1,x}+C_{2,x}*$$

$$(B_{1,x})^2+(B_{1,y})^2=(B_1)^2$$

$$(B_{2,x})^2+(B_{2,y})^2=(B_2)^2$$

$$C_{1,y}=C_{2,y}$$

$$(C_{1,x})^2+(C_{1,y})^2=(C_1)^2$$

$$(C_{2,x})^2+(C_{2,y})^2=(C_2)^2$$

can be solved and will also allow for the calculation of the speed of sound to verify assumptions. As previously mentioned, the foregoing exemplary system of equations is simplified based on the assumption that the container has the same circumference throughout its height.

Figure 7:
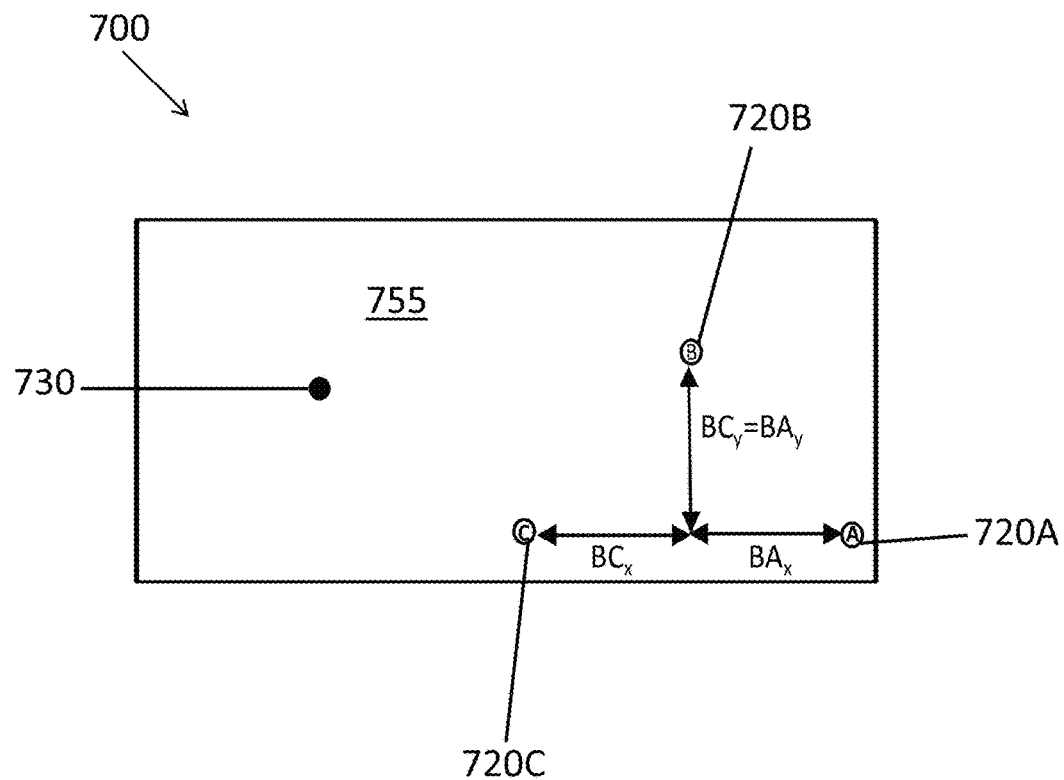
FIG. 7 is a flattened two-dimensional view of an exemplary container volume calibration system according to an embodiment of the present invention.

In one or more exemplary embodiments, an container volume calibration system consisting of two or more sensors with known separations can be used to improve the accuracy of calibration. For example, FIG. 7 is a two dimensional "unwrapped" view of an exemplary container wall 755 and an container volume calibration system 700 including a transducer 730 and sensors 720A, 720B and 720C. FIG. 7 illustrates how a known distance between two sensors (or between the transducer and one sensor) aids in solving the system of equations, and/or calibrating for the speed of sound in the material. In the particular configuration shown in FIG. 7, sensor 720A is attached to the wall of the container in a manner such that BCy=BAy and BCx=BAx and that the longitudinal and transverse distances are also equal to each other.

If all sensors were grouped in this exemplary way, noise from bouncing or other phenomena can be minimized. Furthermore, the system 700 can be configured to calibrate itself and the sensor arrangement can be used to calculate the direction from which any impulse was generated. For instance, directionality of the waves can be calculated using the known distances between sensors and this could be used to ignore any waves propagating from undesirable directions, such as those reflecting from the upper and lower edges of the tank wall. Self-calibration with respect to speed of sound can also be accomplished by considering TOF between two sensors with known spacing and considering the direction of wave propagation. Such additional information can further inform the calculation of container geometry by the control computer 110 and can be used to more accurately determine the volume of the container, for instance, by eliminating bad-data and, optionally, providing localized speed of sound measurements.

Figure 8:
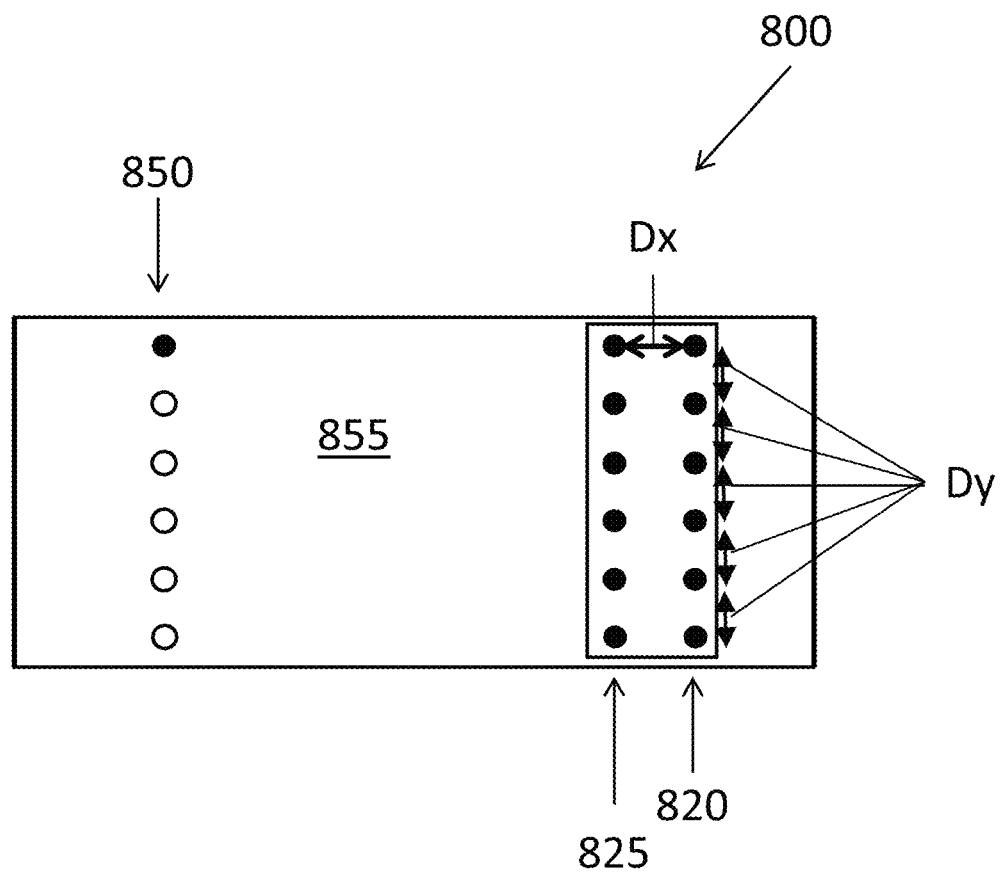
FIG. 8 is a flattened two-dimensional view of an exemplary container volume calibration system according to an embodiment of the present invention.

An exemplary configuration of an container volume calibration system 800 is depicted in FIG. 8, which is an "unwrapped," two-dimensional view of the wall 855 of a cylindrical storage container. As shown, the system 800 comprises two longitudinal rows of sensors (rows 825 and 820) that are arranged such that sets of sensors are provided at respective heights on the wall for which circumference is to be calculated. The system 800 can also includes one or more mobile impulse generators. In some configurations, the transducer(s) could have a mobile configuration (e.g., mounted on a robot) such that they can be moved into position for measuring the container circumference at various levels. In the particular configuration of system 800 shown in FIG. 8, a longitudinal strip 850 including a plurality of transducers is mounted to the wall in a longitudinal orientation. In operation, sensors at each respective height would receive an impulse and the control device (110, not shown) can compensate for any misalignment between the transducer(s) and sensors using the known longitudinal distance (y) between sensors. For instance, such compensation can include determining an average circumference over the small height difference which can be sufficiently accurate, depending on the required accuracy for the application. In addition or alternatively, the height of one or more of the transducers can be longitudinally adjusted until proper longitudinal alignment with the one or more sensors is achieved, as described previously, before proceeding on to the next measurement.

Figure 9:
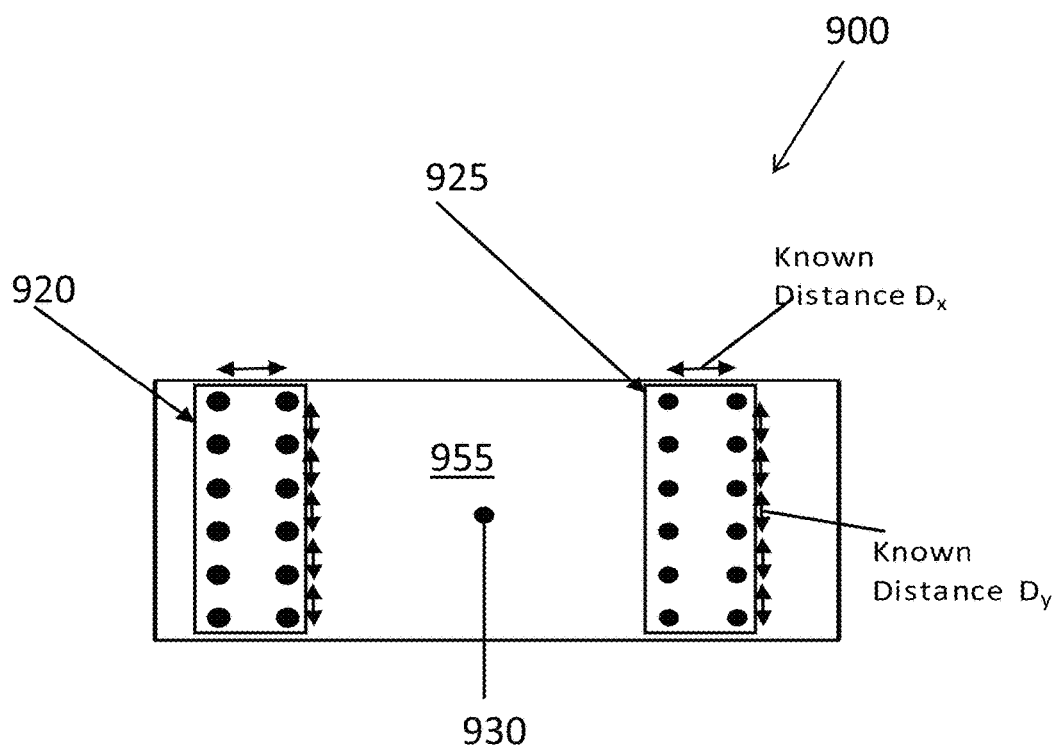
FIG. 9 is a flattened two-dimensional view of an exemplary container volume calibration system according to an embodiment of the present invention.

An exemplary configuration of an container volume calibration system 900 is depicted in FIG. 9, which is an "unwrapped," two-dimensional view of the wall 955 of a cylindrical storage container. The system 900 can be, for example, a long-term installation of the sensors. As shown, the system 900 comprises two sets, or "strips," 925 and 920 that each include two longitudinal rows of sensors that are spaced apart a known distance x in the horizontal direction. Accordingly, each strip is arranged such that two sensors are provided at respective heights on the wall for which circumference is to be calculated. In addition, the sensors are also spaced apart a known distance y in the longitudinal direction. As shown, the system 900 also includes an impulse generator 930.

The exemplary configuration of sensors shown in FIG. 9 can facilitate the determination of circumference with increased accuracy and/or in order to eliminate the need for moving the transducer. For instance, if it was desirable to have a single stationary impulse generator, as opposed to higher accuracy from using a mobile transducer, the measurement of circumference can be derived by determining the position of each sensor in three dimensional space and then using two sensors having the same level as the transducer to calculate the diameter of the container at that level. Accordingly, the control computer can be configured to, using a single pulse, calculate the diameter of each level containing a pair of opposing sensors, and thus determine the corresponding circumferences and/or the total volume of the container. Such an exemplary system configuration would be beneficial in cases where frequent monitoring is desired. Moreover, it is worth noting that the calculation of the container geometry can be further simplified by virtue of placing the two sets of sensors on the surface 955 such that they are located at approximately opposite sides of the container (e.g., have a generally equal circumferential distance between 920 and 926 about the cylindrical container in both the clockwise and counter clockwise directions).

At this juncture, it should be noted that although much of the foregoing description has been directed to systems and methods for calibration of the volume of storage containers, the systems and methods disclosed herein can be similarly deployed and/or implemented in scenarios, situations, and settings far beyond the referenced scenarios. For instance, the exemplary systems and methods can be adapted to measure the volume of containers using various types of mechanical waves and without limitation to acoustic devices.

It should be appreciated that more or fewer operations can be performed than shown in the figures and described. These operations can also be performed in a different order than those described. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a system and a computer implemented method, computer system, and computer program product for calibration of the volume of storage containers. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A method of measuring a volume of a storage container using a plurality of acoustic devices, the plurality of acoustic devices including a transducer and one or more sensors, the method comprising:
    deploying the plurality of acoustic devices into respective positions on an exterior surface of a circumferential wall of the container, wherein the one or more sensors are acoustically coupled to the surface and configured to detect pulses propagating along the surface, and wherein the transducer is acoustically coupled to the surface and is configured generate one or more pulses that radiate along the surface away from the transducer and toward the one or more sensors in at least a first circumferential path and a second circumferential path;
    generating one or more pulses using the transducer, wherein each pulse is generated at an impulse time;
    detecting, using the one or more sensors, the one or more pulses radiating along the first circumferential path, and the second circumferential path and recording a respective time that the one or more pulses radiating along a respective circumferential path are detected;
    calculating, by a computing device in electronic communication with the one or more sensors based on the impulse time and respective detection times, respective times of flight (TOFs) for the one or more pulses, wherein each respective TOF is an elapsed time for the pulse to travel between two of the acoustic devices along a particular circumferential path;
    aligning at least two of the acoustic devices in one or more of a transverse and longitudinal direction relative to the circumferential wall of the container based on the calculated TOFs;
    calculating, with the computing device, respective distances between the acoustic devices in each of the first and second circumferential directions based on the respective TOFs and a speed of sound through the wall; and
    determining, with the computing device, the volume of the storage container based on the calculated respective distances.

2. The method of claim 1, wherein deploying the plurality of acoustic devices comprises deploying at least a first acoustic sensor and a second acoustic sensor at respective positions that are separated by a known distance, and further comprising the steps of:
    calculating, with the computing device, a TOF for the pulse radiating between the first and second acoustic sensors having the known separation distance; and
    calculating, with the computing device, the speed of sound through the wall based on the TOF of the pulse radiating between the first and second acoustic sensors and the known separation distance.

3. The method of claim 1, wherein the step of aligning comprises:
    iteratively adjusting the respective position of one or more of the acoustic devices on the surface in one or more of the transverse and longitudinal directions, and
    repeating the steps of generating, detecting and calculating TOFs until one or more re-calculated TOFs indicate that the respective positions of at least two of the acoustic devices are aligned in one or more of a transverse and longitudinal direction.

4. The method of claim 3, wherein the deploying step comprises deploying the one or more acoustic devices at respective positions on the surface using one or more robots that are operated under the control of the computing device.

5. The method of claim 3, wherein the step of iteratively adjusting the respective position of one or more of the acoustic devices comprises:
moving the transducer a prescribed amount in the longitudinal direction using the computing device and a robot, wherein the respective position of the transducer and the prescribed amount is measured in near-real time using one or more position sensors on-board the robot.

6. The method of claim 1, wherein deploying the plurality of sensors on the surface of the container at respective positions comprises deploying the plurality of sensors at different respective heights on the surface of the container;
incrementally re-positioning the transducer in the longitudinal direction along the surface of the container using a robot;
repeating the steps of generating, detecting and calculating TOFs for the one or more pulses for each position of the transducer;
wherein the step of aligning includes, determining, based on the calculated TOFs, whether the transducer is aligned with one or more of the sensors in the longitudinal direction; and
calculating, based on the calculated TOFs, the circumference of the container at each position in which the transducer is determined to be in alignment with one or more of the plurality of sensors.

7. A system for measuring a volume of a storage container, the system comprising:
a plurality of acoustic devices configured to be deployed at respective positions on an exterior surface of a circumferential wall of the container, the acoustic devices including:
a plurality of sensors configured to be acoustically coupled to the circumferential wall and to detect pulses radiating along the surface,
a transducer configured to be acoustically coupled to the surface and generate one or more pulses that radiate along the surface away from, the transducer and toward the plurality of sensors along respective circumferential paths;
a robot configured to deploy one or more of the acoustic devices on the surface of the circumferential wall, wherein the robot includes a drive system and one or more position sensors for monitoring a position of the robot, wherein the robot is configured to controllably deploy the one or more acoustic devices on the surface; and
a control computing system comprising:
a non-transitory computer readable storage medium,
one or more processors in electronic communication with the plurality of acoustic devices, the robot and the computer readable storage medium,
one or more software modules comprising executable instructions stored in the storage medium, wherein the one or more software modules are executable by the processor and include:
a signal control module that configures the processor to, using the transducer, generate one or more pulses using the transducer at respective impulse times, wherein the signal control module further configures the processor to, using the sensors, detect the arrival of the one or more pulses at the sensors, respectively, and record respective detection times,
a signal analysis module that configures the processor to calculate, based on the respective impulse times and respective detection times, respective times of flight (TOFs) for the one or more pulses, wherein respective TOFs are an elapsed time for the pulse to travel between two of the acoustic devices along a respective circumferential path,
a geometric analysis module that configures the processor to calculate distances between the acoustic devices based on the respective TOFs and a speed of sound through the wall, and to calculate the volume of the storage container based on the calculated distances, and
a position control module, among the software modules, wherein the position control module configures the processor to, using the robot, iteratively adjust the respective position of the transducer on the surface in the longitudinal direction and re-calculate respective TOFs until the transducer is aligned in the longitudinal direction with at least one of the acoustic sensors, wherein alignment achieved when a minimum re-calculated TOF of a pulse traveling between the transducer and the at least one sensor is identified by the processor.

8. The system of claim 7, wherein the plurality of sensors include at least a first acoustic sensor and a second acoustic sensor deployed at respective positions that are separated by a known distance in one or more of the longitudinal direction and transverse direction.

9. The system of claim 8, wherein the signal analysis module further configures the processor to calculate a TOF for the pulse radiating between the first and second acoustic sensors having the known separation distance and further configures the processor to calculate the speed of sound through the wall based on the TOF of the pulse radiating between the first and second acoustic sensors and the known separation distance.

10. A system for measuring a volume of a storage container, the system comprising:
a plurality of acoustic devices configured to be deployed at respective positions on an exterior surface of a circumferential wall of the container, the acoustic devices including:
a plurality of sensors configured to be acoustically coupled to the circumferential wall at respective positions that are separated by a known distance in one or more of the longitudinal direction and transverse direction and configured to detect pulses radiating along the surface, wherein the plurality of sensors include an array of acoustic sensors, the array including at least two parallel longitudinal rows of acoustic sensors, and the wherein acoustic sensors in a longitudinal row are spaced apart a known longitudinal spacing, and wherein the two rows are spaced apart in the transverse direction a known transverse spacing, and
a transducer configured to be acoustically coupled to the surface and generate one or more pulses that radiate along the surface away from the transducer and toward the plurality of sensors along respective circumferential paths; and
a control computing system comprising;
a non-transitory computer readable storage medium,
one or more processors in electronic communication with the plurality of acoustic devices, and the computer readable storage medium,
one or more software modules comprising executable instructions stored in the storage medium, wherein the one or more software modules are executable by the processor and include:
a signal control module that configures the processor to, using the transducer, generate one or more pulses using the transducer at respective impulse times, wherein the signal control module further configures the processor to, using the sensors, detect the arrival of the one or more pulses at the sensors respectively, and record respective detection times,
a signal analysis module that configures the processor to calculate, based on the respective impulse times and respective detection times, respective times of flight (TOFs) for the one or more pulses, wherein respective TOFs are an elapsed time for the pulse to travel between two of the acoustic devices along a respective circumferential path, and
a geometric analysis module that configures the processor to calculate distances between the acoustic devices based on the respective TOFs and a speed of sound through the wall, and to calculate the volume of the storage container based on the calculated distances.

11. The system of claim 10, further comprising:
a robot configured to deploy one or more of the acoustic devices on the surface of the circumferential wall, wherein the robot includes a drive system and one or more position sensors for monitoring a position of the robot, wherein the robot is configured to controllably deploy the one or more acoustic devices on the surface.

12. The system of claim 10, wherein the transducer is one of a stationary transducer and a mobile transducer.

13. The system of claim 10, further comprising, a plurality of transducers mounted to the wall and spaced apart in the longitudinal direction.

14. The system of claim 10, wherein the geometric analysis module configures the processor to, using a pulse, calculate the circumference of the container at respective longitudinal levels of the plurality of sensors and compensate for any misalignment between the transducer and one or more of the sensors as a function of the known distance between sensors in the longitudinal direction.

15. The system of claim 10, wherein two rows of acoustic sensors are positioned at opposite sides of the container such the rows are spaced apart by a circumferential distance about the container that is generally equal in both a clockwise and counter clockwise directions.

16. A system for measuring a volume of a storage container, the system comprising:
a plurality of acoustic devices configured to be deployed at respective positions on an exterior surface of a circumferential wall of the container, the acoustic devices including:
a plurality of sensors configured to be acoustically coupled to the circumferential wall and to detect pulses radiating along the surface,
a transducer configured to be acoustically coupled to the surface and generate one or more pulses that radiate along the surface away from the transducer and toward the plurality of sensors along respective circumferential paths;
a robot configured to deploy one or more of the acoustic devices on the surface of the circumferential wall, wherein the robot includes a drive system and one or more position sensors for monitoring a position of the robot, wherein the robot is configured to controllably deploy the one or more acoustic devices on the surface; and
a control computing system comprising:
a non-transitory computer readable storage medium,
one or more processors in electronic communication with the plurality of acoustic devices, the robot and the computer readable storage medium,
one or more software modules comprising executable instructions stored in the storage medium, wherein the one or more software modules are executable by the processor and include:
a signal control module that configures the processor to, using the transducer, generate one or more pulses using the transducer at respective impulse times, wherein the signal control module further configures the processor to, using the sensors, detect the arrival of the one or more pulses at the sensors, respectively, and record respective detection times,
a signal analysis module that configures the processor to calculate, based on the respective impulse times and respective detection times, respective times of flight (TOFs) for the one or more pulses, wherein respective TOFs are an elapsed time for the pulse to travel between two of the acoustic devices along a respective circumferential path,
a geometric analysis module that configures the processor to calculate distances between the acoustic devices based on the respective TOFs and a speed of sound through the wall, and to calculate the volume of the storage container based on the calculated distances, and
a position control module that configures the processor to, using the robot, iteratively adjust the respective position of one or more of the acoustic devices on the surface and re-calculate respective TOFs until at least two of the acoustic devices are aligned in one of a transverse direction and a longitudinal direction, wherein the processor is configured to control alignment of at least two of the acoustic devices in one or more of a transverse and longitudinal direction relative to the circumferential wall of the container based on the calculated TOFs, and wherein alignment of the at least two devices is achieved when the re-calculated TOF of a pulse radiating between the at least two acoustic devices is minimized.

17. The system of claim 16, wherein the plurality of sensors include at least a first acoustic sensor and a second acoustic sensor deployed at respective positions that are separated by a known distance in one or more of the transverse direction and the longitudinal direction.

18. The system of claim 17, wherein the signal analysis module further configures the processor to calculate a TOF for the pulse radiating between the first and second acoustic sensors having the known separation distance and further configures the processor to calculate the speed of sound through the wall based on the TOF of the pulse radiating between the first and second acoustic sensors and the known separation distance.

19. The system of claim 16, wherein the position control module configures the processor to adjust the position of the transducer a prescribed amount in the longitudinal direction until the transducer is aligned with one or more of the plurality of sensors.

20. The system of claim 19, wherein the processor is configured to calculate the circumference of the container for each position in which the transducer is aligned with the one or more of the plurality of sensors.

* * * * *